(12) United States Patent
Mizuno et al.

(10) Patent No.: US 6,187,772 B1
(45) Date of Patent: Feb. 13, 2001

(54) PYRROLOAZEPINE COMPOUNDS

(75) Inventors: Akira Mizuno, Kyoto; Makoto Shibata, Ashikaga; Tomoe Kamei, Takatsuki; Norio Inomata, Mino, all of (JP)

(73) Assignee: Suntory Limited, Osaka (JP)

( * ) Notice: Under 35 U.S.C. 154(b), the term of this patent shall be extended for 0 days.

(21) Appl. No.: 09/147,248

(22) PCT Filed: Mar. 16, 1998

(86) PCT No.: PCT/JP98/01085

§ 371 Date: Nov. 12, 1998

§ 102(e) Date: Nov. 12, 1998

(87) PCT Pub. No.: WO98/41527

PCT Pub. Date: Sep. 24, 1998

(30) Foreign Application Priority Data

Mar. 14, 1997 (JP) .................................................. 9-079246

(51) Int. Cl.⁷ ..................... C07D 487/04; A61K 31/496; A61K 31/4523
(52) U.S. Cl. ............................................. 514/215; 540/521
(58) Field of Search ............................... 540/521; 514/215

(56) References Cited

U.S. PATENT DOCUMENTS

| | | |
|---|---|---|
| 5,206,239 | 4/1993 | Mizuno et al. . |
| 5,391,731 | 2/1995 | Mizuno et al. ........................ 514/215 |
| 5,397,780 | 3/1995 | Mizuno et al. ........................ 514/215 |
| 5,399,557 | 3/1995 | Mizuno et al. ........................ 514/215 |
| 5,416,082 | 5/1995 | Mizuno et al. ........................ 514/215 |
| 5,684,161 | 11/1997 | Imoto et al. ........................... 548/531 |

*Primary Examiner*—Bruck Kifle
(74) *Attorney, Agent, or Firm*—Oblon, Spivak, McClelland, Maier & Neustadt, P.C.

(57) ABSTRACT

Disclosed are pyrroloazepine compounds and their salts. These pyrroloazepine compounds are represented by formula (I) wherein the dashed line indicates the presence or absence of a bond; and, when the bond is present, $Z_2$ is not present and $Z_1$ is H but, when the bond is absent, $Z_1$ and $Z_2$ are both Hs; $Z_1$ is H and $Z_2$ is OH; $Z_1$ and $Z_2$ are both $SR_5$s in which $R_5$ is alkyl, aralkyl or aryl; or $Z_1$ and $Z_2$ are combined together to represent O, $NOR_6$ in which $R_6$ is H, alkyl, aralkyl or aryl, or $C_2$–$C_3$ alkylenedithio; R is H, alkyl, cycloalkyl, cycloalkyl alkyl or aralkyl; and the ring P is a specific pyrrole ring. These pyrroloazepine compounds and salts are effective as preventives or therapeutics for general circulatory diseases such as hypertension, heart failure, ischemic hear diseases, cerebrovascular disturbances and peripheral circulatory disturbances. Their production processes are also disclosed

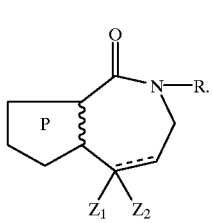

(I)

21 Claims, No Drawings

PYRROLOAZEPINE COMPOUNDS

TECHNICAL FIELD

This invention relates to novel pyrroloazepine compounds. More specifically, this invention is concerned with pyrrolo[3,2-c]azepine compounds, pyrrolo-[3,4-c]azepine compounds and salts thereof, said compounds and salts having strong $\alpha_1$-blocking action and serotonin-2 receptor antagonistic action and being useful as pharmaceuticals for use in the prevention or treatment of circulatory diseases such as hypertension, heart failure, ischemic heart diseases such as angina pectoris, myocardial infarction and post-PTCA restenosis, cerebrovascular disturbances such as cerebral infarction and cerebral sequelae after sub-arachnoid hemorrhage, and peripheral circulatory disturbances such as arteriosclerosis obliterans, thromboangiitis obliterans, Raynaud disease and Buerger disease; their preparation process; and pharmaceuticals containing them as effective ingredients.

BACKGROUND ART

As pharmaceuticals which act on the circulatory system, many products are known to date, including a variety of products developed as vasodilators.

Among such vasodilators, $\alpha_1$-blockers led by prazosin are the targets of active developments, because they have advantages such that (1) their anti-hypertensive action is strong and reliable, (2) they do not adversely affect lipometabolism or saccharometabolism and (3) they can be used easily for hypertensives suffering from complication. As $\alpha_1$-blockers which are currently in clinical use, bunazosin, terazosin, urapidil, doxazosin and the like can be mentioned in addition to prazosin. Further, medicines having $\alpha_1$-blocking action and anti-serotonin action in combination are expected to become still better therapeutics for hypertension, because they have possibility to reduce side effects, such as orthostatic hypotension and reflex tachycardia, induced by anti-hypertensive action which is based on $\alpha_1$-blocking action.

Further, a hypertensive is considered to be prone to an ischemic heart disease or peripheral circulatory disturbance, since his or her platelet aggregating ability has been generally potentiated to have higher thrombophilia. As one of those taking part in thrombosis, serotonin is known. Serotonin is a compound contained abundantly in platelets, which are a blood component, and in a central nervous system, on the other hand, it acts as a neurotransmitter. In platelets, it is released upon stimulation by thromboxane $A_2$, ADP, collagen or the like, and synergistically acts on release of various platelet aggregation factors through activation of serotonin-2 receptors in the platelets and vascular smooth muscle cells and also on vasoconstriction by norepinephrine through $\alpha_1$ receptors, thereby inducing strong platelet aggregation and vasoconstriction [P.M. Vanhoutte, "Journal of Cardiovascular Pharmacology", Vol. 17 (Suppl. 5), S6–S12 (1991)].

Serotonin is also known to potentiate proliferation of vascular smooth muscle cells [S. Araki et al., "Atherosclerosis", Vol. 83, pp.29–34(1990)]. It has been considered that, particularly when endothelial cells are injured as in arteriosclerosis or myocardial infarction, the vasoconstricting action and thrombus forming action of serotonin are exasperated, thereby reducing or even stopping blood supply to myocardial, cerebral and peripheral organs [P. Golino et al., "The New England Journal of Medicine", Vol. 324, No. 10, pp. 641–648(1991), Y. Takiguchi et al., "Thrombosis and Haemostasis", Vol. 68(4), pp. 460–463 (1992), A. S. Weyrich et al., "American Journal of Physiology", Vol. 263, H349–H358(1992)]. Being attracted by such actions of serotonin or serotonin-2 receptors, various attempts are now under way to use a serotonin-2 receptor antagonist as a pharmaceutical for ischemic diseases of the heart, the brain and peripheral tissues.

From the foregoing, a medicine having $\alpha_1$-blocking action and serotonin-2 receptor antagonistic action in combination is expected to have vasodilative action, antiplatelet action and vascular smooth muscle proliferation inhibiting action, and is considered to become a medicine extremely effective for the prevention or treatment of not only hypertension but also general circulatory diseases such as heart failure, ischemic heart diseases such as angina pectoris, myocardial infarction and post-PTCA restenosis, cerebrovascular disturbances such as cerebral infarction and cerebral sequelae after subarachnoid hemorrhage, and peripheral circulatory disturbances such as arteriosclerosis obliterans, thromboangiitis obliterans, Raynaud disease and Buerger disease.

Until today, several medicines have been reported to have $\alpha_1$-blocking action and serotonin-2 receptor antagonistic action in combination. They are however still accompanied with many problems to be improved in potency, selectivity to other receptors, toxicity, side effects and the like. There is hence an outstanding desire for the provision of a still better compound.

DISCLOSURE OF THE INVENTION

In view of the foregoing circumstances, the present inventors have proceeded with extensive research, resulting in the finding of pyrrolo[3,2-c]azepine compounds and pyrrolo[3,4-c]azepine compounds which have strong $\alpha_1$-blocking action and serotonin-2 receptor antagonistic action in combination, have low toxicity and less side effects, and are useful for the prevention and treatment of general circulatory diseases such as hypertension, heart failure, ischemic heart diseases, cerebrovascular disturbances and peripheral circulatory disturbances.

The present invention has been completed based on the above described findings. A first object of the present invention is to provide a pyrroloazepine compound or a salt thereof, said pyrroloazepine compound being represented by the following formula (I):

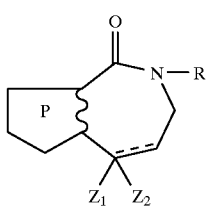

(I)

wherein the ring P represented by

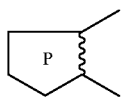

means a pyrrole ring represented by the following structure:

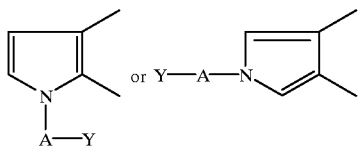

in which A represents an alkylene group, an alkenylene group or an alkynylene group, and Y represents a group

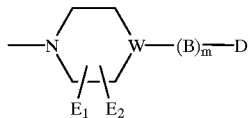

in which W represents CH, C= or a nitrogen atom; and, when W represents CH, m stands for 0 or 1, B represents an oxygen atom, a sulfur atom, a carbonyl group, a sulfinyl group, a sulfonyl group, an alkylene group, an alkenylene group, a group —C(OH)$R_1$— in which $R_1$ represents a substituted or unsubstituted aryl group, a group —CHR$_2$— in which $R_2$ represents a substituted or unsubstituted aryl group, or a substituted or unsubstituted, cyclic or acyclic acetal group; when W represents C=, m stands for 1, B represents a group

in which the double bond is coupled with W and $R_3$ represents a substituted or unsubstituted aryl group or a substituted or unsubstituted aralkyl group; when W represents a nitrogen atom, m stands for 0 or 1, and B represents a carbonyl group, a sulfonyl group, an alkylene group, an alkenylene group or a group —CHR$_4$— in which $R_4$ represents a substituted or unsubstituted aryl group; $E_1$ and $E_2$ each independently represents a hydrogen atom or a lower alkyl group; and D represents a substituted or unsubstituted aromatic hydrocarbon group or a substituted or unsubstituted aromatic heterocyclic group;

the dashed line indicates the presence or absence of a bond; and, when the bond indicated by the dashed line is present, $Z_2$ is not present and $Z_1$ represents a hydrogen atom but, when the bond indicated by the dashed line is absent, $Z_1$ and $Z_2$ both represent hydrogen atoms; $Z_1$ represents a hydrogen atom and $Z_2$ represents a hydroxyl group; $Z_1$ and $Z_2$ both represent groups SR$_5$ in which $R_5$ represents a substituted or unsubstituted alkyl group, a substituted or unsubstituted aralkyl group or a substituted or unsubstituted aryl group; or $Z_1$ and $Z_2$ are combined together to represent an oxygen atom, a group NOR$_6$ in which $R_6$ represents a hydrogen atom, a substituted or unsubstituted alkyl group, a substituted or unsubstituted aralkyl group or a substituted or unsubstituted aryl group, or a group

in which G represents stituted or unsubstituted ethylene group or a substituted or unsubstituted trimethylene group; and R represents a hydrogen atom, a linear or branched alkyl group, a cycloalkyl group, a cycloalkylalkyl group or a substituted or unsubstituted aralkyl group.

A second object of the present invention is to provide a preparation process of the pyrroloazepine compound (I) or its salt.

Further, a third object of the present invention is to provide a pharmaceutical which comprises the pyrroloazepine compound (I) or its pharmacologically-acceptable salt as an effective ingredient and is usable for the treatment or the like of circulatory diseases.

BEST MODES FOR CARRYING OUT THE INVENTION

In the pyrroloazepine compound (I) of the present invention, preferred examples of the group R can include a hydrogen atom; linear or branched alkyl groups having 1–8 carbon atoms preferably, such as methyl, ethyl, n-propyl, isopropyl and n-pentyl; cycloalkyl groups having 3–8 carbon atoms, such as cyclopropyl, cyclopentyl and cyclohexyl; cycloalkyl-alkyl groups having 4–8 carbon atoms, such as cyclopropylmethyl, cyclohexylmethyl and cyclohexylethyl; and aralkyl groups having 7–22 carbon atoms, such as diphenylmethyl, benzyl and phenethyl. One or more hydrogen atoms of each of these groups may be substituted by a like number of halogen atoms such as fluorine, chlorine and/or bromine atoms, alkyl groups having 1–4 carbon atoms preferably, such as methyl and/or ethyl, and/or alkoxy groups having 1–4 carbon atoms preferably, such as methoxy and/or ethoxy. Particularly preferred examples of the group R can be methyl and ethyl.

Further, preferred examples of the group $Z_1$ and the group $Z_2$ in the compound (I) according to the present invention can include the following combinations: when the bond indicated by the dashed line is present, $Z_2$ is not present and $Z_1$ represents a hydrogen atom; when the bond indicated by the dashed line is absent, $Z_1$ and $Z_2$ are both hydrogen atoms, $Z_1$ and $Z_2$ both represent the groups SR$_5$, $Z_1$ represents a hydrogen atom and $Z_2$ represents a hydroxyl group, and $Z_1$ and $Z_2$ are combined together to represent an oxygen atom, the group NOR$_6$ or the group

wherein G has the same meaning as defined above.

Preferred examples of $R_6$ in the group NOR$_6$ can include a hydrogen atom; linear or branched alkyl groups having 1–4 carbon atoms preferably, such as methyl and ethyl; aryl groups having 6–14 carbon atoms, such as phenyl and naphthyl; and aralkyl groups having 7–22 carbon atoms, such as benzyl and phenethyl. One or more of the hydrogen atoms of each of these groups may be substituted by a like number of halogen atoms such as fluorine, chlorine and/or bromine atoms, alkyl groups having 1–4 carbon atoms preferably, such as methyl and/or ethyl, and/or alkoxy groups having 1–4 carbon atoms preferably, such as methoxy and/or ethoxy. Of these, hydrogen atom and methyl group are particularly preferred.

Further, preferred examples of G in the group

can include ethylene and trimethylene. One or more of the hydrogen atoms of each of these groups may be substituted by a like number of halogen atoms such as fluorine, chlorine and/or bromine atoms, alkyl groups having 1–4 carbon atoms preferably, such as methyl and/or ethyl, aryl groups having 6–14 carbon atoms, such as phenyl and naphthyl, aralkyl groups having 7–22 carbon atoms, such as benzyl and phenethyl, and/or alkylidene groups having 1–4 carbon atoms preferably, such as methylidene and/or ethylidene.

Preferred examples of $R_5$ in the group $SR_5$ can include linear or branched alkyl groups having 1–4 carbon atoms preferably, such as methyl and ethyl; aryl groups having 6–14 carbon atoms such as phenyl and naphthyl; and aralkyl groups having 7–22 carbon atoms such as benzyl and phenethyl. One or more of the hydrogen atoms of each of these groups may be substituted by a like number of halogen atoms such as fluorine, chlorine and/or bromine atoms, alkyl groups having 1–4 carbon atoms preferably, such as methyl and/or ethyl, and/or alkoxy groups having 1–4 carbon atoms preferably, such as methoxy and/or ethoxy.

In the pyrroloazepine compounds (I) of the present invention, the ring P represents any one of the following pyrrole rings:

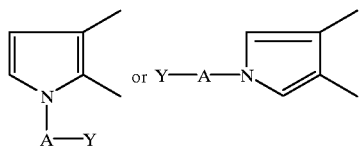

wherein A and Y have the same meanings as defined above.

Preferred examples of the group A can include linear or branched alkylene groups having 2–10 carbon atoms, such as ethylene, trimethylene, tetramethylene, pentamethylene and octamethylene; linear or branched alkenylene groups having 4–10 carbon atoms, such as 2-butenylene and 3-pentenylene; and linear or branched alkynylene groups having 4–10 carbon atoms, such as 2-butynylene and 3-pentynylene. One or more of the hydrogen atoms of each of these groups may be substituted by a like number of halogen atoms such as fluorine, chlorine and/or bromine atoms. Among the above groups, trimethylene, tetramethylene and pentamethylene are particularly preferred.

In the ring P, Y is a group

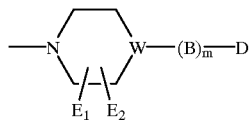

wherein B, D, $E_1$, $E_2$, W and m have the same meanings as defined above. The group, which is contained in the above group and is represented by the following formula:

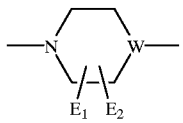

wherein $E_1$, $E_2$ and W have the same meanings as defined above, is a heterocyclic group derived from piperidine or piperazine, and two or less of the hydrogen atoms on the ring may be substituted by a like number of alkyl groups having 1–4 carbon atoms preferably, such as methyl and/or ethyl.

When the above group is a heterocyclic group derived from piperidine, m stands for 0 or 1 (with the proviso that m stands for 1 when Y represents C=), and B represents an oxygen atom, a sulfur atom, a carbonyl group, a sulfinyl group, a sulfonyl group, an alkylene group (an alkylene group having 1–4 carbon atoms preferably, with a methylene group being particularly preferred), an alkenylene group (an alkenylene group having 2–5 carbon atoms preferably, with a 2-propenylene group being particularly preferred), a group —C(OH)$R_1$— in which $R_1$ represents an aryl group having 6–14 carbon atoms, such as phenyl or naphthyl, and one or more hydrogen atoms may be substituted, a group —CHR$_2$— in which $R_2$ represents an aryl group having 6–14 carbon atoms, such as phenyl or naphthyl, and one or more hydrogen atoms may be substituted, a group

in which the double bond is coupled with W, $R_3$ represents an aryl group having 6–14 carbon atoms, such as phenyl or naphthyl, or an aralkyl group having 7–22 carbon atoms, such as benzyl or phenethyl, and these groups may be in substituted forms, or a cyclic or acyclic acetal group in which one or more of the hydrogen atoms may be substituted.

Examples of the cyclic or acyclic acetal group can include:

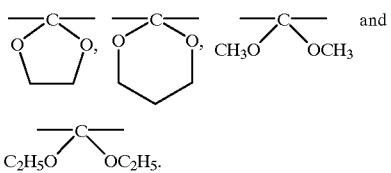

In the above-described definition of B, preferred examples of the substituents for the groups $R_1$, $R_2$ can include alkyl groups having 1–4 carbon atoms preferably, such as methyl and ethyl; and aryl groups having 6–14 carbon atoms, such as phenyl and naphthyl. These groups may be substituted by one or more of halogen atoms such as fluorine, chlorine and/or bromine, alkoxy groups having 1–4 carbon atoms preferably, such as methoxy and/or ethoxy, hydroxyl groups, cyano groups, nitro groups and the like.

Exemplary substituents for $R_3$ can include one or more of halogen atoms such as fluorine, chlorine and/or bromine, alkyl groups having 1–4 carbon atoms preferably, such as methyl and/or ethyl, alkoxy groups having 1–4 carbon atoms preferably, such as methoxy and/or ethoxy, and hydroxyl groups. Illustrative of the substituent for the cyclic or acyclic acetal can be halogen atoms such as fluorine, chlorine and bromine, alkyl groups having 1–4 carbon atoms preferably, such as methyl and ethyl, aryl groups having 6–14 carbon atoms, such as phenyl and naphthyl, aralkyl groups having 7–22 carbon atoms, such as benzyl and phenethyl, and alkylidene groups having 1–4 carbon atoms preferably, such as methylidene and ethylidene.

Among these examples of B, particularly preferred is a carbonyl group.

When the heterocyclic group is a group derived from piperazine, m stands for 0 or 1 (preferably 0), and B represents a carbonyl group, a sulfonyl group, an alkylene group (preferably, an alkylene group having 1–4 carbon atoms, with a methylene group being particularly preferred), an alkenylene group (preferably, an alkenylene group having 3–6 carbon atoms, with a 2-propenylene group being particularly preferred), a group —$CHR_4$— in which $R_4$ represents an aryl group having 6–14 carbon atoms, such as phenyl or naphthyl.

The above-described $R_4$ may be substituted further by one or more of halogen atoms such as fluorine, chlorine and/or bromine, alkyl groups having 1–4 carbon atoms preferably, such as methyl and/or ethyl, and/or alkoxy groups having 1–4 carbon atoms preferably, such as methoxy and/or ethoxy.

Among the above-described examples of B, preferred is a substituted or unsubstituted phenylmethylene group.

Preferred examples of D can include aromatic hydrocarbon groups having 6–28 carbon atoms preferably, such as a phenyl group in which one or more of the hydrogen atoms may be substituted and a naphthyl group in which one or more of the hydrogen atoms may be substituted.

Other preferred examples of D can include aromatic heterocyclic groups, preferably those each of which is monocyclic or dicyclic and contains three or less hetero atoms, such as pyridyl, pyrimidinyl, benzisothiazolyl, benzisoxazolyl, indazolyl and indolyl groups in which one or more of hydrogen atoms may be substituted. Illustrative of the hetero atoms can be oxygen, sulfur and/or nitrogen atoms.

Examples of the substituents for the above aromatic hydrocarbon group or aromatic heterocyclic group can include halogen atoms such as fluorine, chlorine and bromine; alkyl groups having 1–4 carbon atoms preferably, such as methyl and ethyl; alkoxy groups having 1–4 carbon atoms preferably, such as methoxy and ethoxy; aryl groups having 6–14 carbon atoms, such as phenyl and naphthyl; aralkyl groups having 7–22 carbon atoms, such as benzyl and phenethyl; aralkyloxy groups having 7–22 carbon atoms preferably, such as benzyloxy; cyano groups; nitro groups; carboxyl groups; alkoxycarbonyl groups (with an alcohol moiety thereof having 1–6 carbon atoms preferably); lower alkylsulfonylamino groups (with an alkyl moiety thereof having 1–4 carbon atoms preferably); carbamoyl groups; and hydroxyl groups.

Among these examples of group D, preferred ones can include phenyl groups which may be unsubstituted or substituted by one or more of halogen atoms, alkoxy groups and/or hydroxyl groups; benzisothiazolyl groups which may be unsubstituted or substituted by one or more halogen atoms; benzisoxazolyl groups which may be unsubstituted or substituted by one or more halogen atoms; and indazolyl groups which may be unsubstituted or substituted by one or more halogen atoms. Particularly preferred are an unsubstituted phenyl group; and phenyl groups substituted by one or more of fluorine atoms, methoxy groups and/or hydroxyl groups.

Many of the compounds (I) according to the present invention have isomers. It is to be noted that these isomers and mixtures thereof are all embraced by the present invention.

Various processes can be employed for the preparation of the pyrroloazepine compounds (I) according to the present invention. It is however preferred to prepare them, for example, by any one of the processes to be described as Process 2 onwards while using as starting material pyrroloazepine compounds (II) or (II') available by Process 1 which will be described hereinafter.

Process 1

The pyrroloazepine compounds (II) and (II') useful as starting materials can be synthesized, for example, by the following process:

Each compound of the formula (II) or the formula (II') can be obtained in accordance with the following reaction scheme, namely, by reacting a pyrrole-3-carboxylic acid or a derivative thereof represented by the formula (XV) with a β-aminopropionic acid or a derivative thereof represented by the formula (XVI') or an organic or inorganic salt thereof and, if necessary, conducting deprotection to obtain a compound represented by the formula (XVII') and then subjecting the thus-obtained compound to a ring-closing reaction.

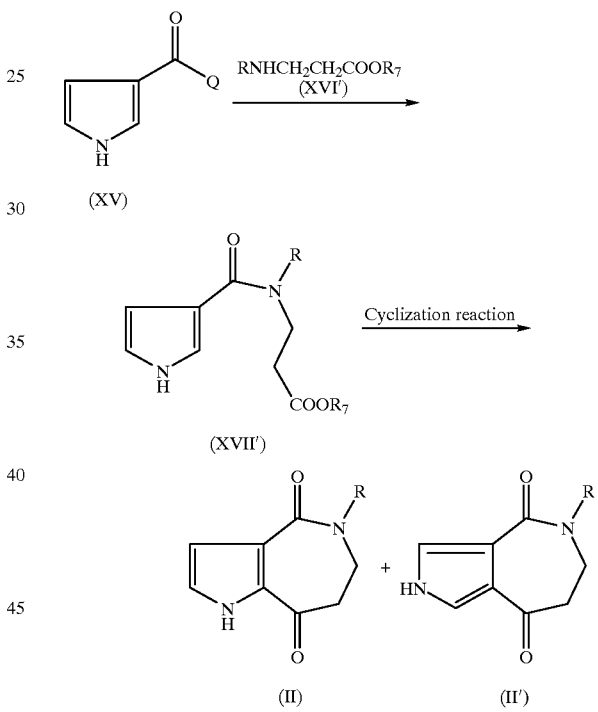

wherein Q represents a hydroxyl group, an alkoxy group or an eliminative group easily replaceable by an amino group, and R and $R_7$ have the same meanings as defined above.

Examples of the eliminative group, which is easily replaceable with an amino group and is represented by the group Q in the compound (XV), can include halogen atoms, an acyloxy group and a p-nitrophenoxy group. On the other hand, as the carboxyl-protecting group represented by the group $R_7$ in the compound (XVI'), it is possible to use, in addition to lower alkyl groups such as methyl, ethyl, n-propyl, isopropyl, n-butyl, isobutyl and t-butyl and aralkyl groups having 7–20 carbon atoms, such as benzyl and 9-anthrylmethyl, conventional protecting groups such as those described in T. W. Greene: "Protective Groups in Organic Synthesis" (John Wiley & Sons, Inc.) and the like.

For the synthesis of the compound (XVII'), it is possible to use any one of various processes disclosed in "Compendium of organic Synthetic Methods" (WILEY-INTERSCIENCE; A Division of John Wiley & Sons, Inc.) and the like.

Illustrative synthesis processes of the compound (XVII') can include a process in which a pyrrole-3-carboxylic acid [the compound (XV) in which Q=OH] and a β-aminopropionic acid or a derivative thereof represented by the formula (XVI') or an organic or inorganic salt thereof are treated with an organic compound such as diethyl phosphorocyanidate (DEPC), diphenylphosphoryl azide (DPPA), dicyclohexylcarbodiimide (DCC), 1-ethyl-3-(3-dimethylaminopropyl)-carbodiimide hydrochloride or 2-iodo-1-methylpyridinium iodide or an inorganic compound such as silicon tetrachloride or tin tetrachloride, if necessary, in the presence of an organic or inorganic base; and a process in which a pyrrole-3-carboxylic acid is converted into its acid halide, symmetric acid anhydride, mixed acid anhydride, its active ester such as p-nitrophenyl ester, or the like by a method known per se in the art, and is then reacted with the compound (XVI'), if necessary, in the presence of an organic or inorganic base.

Each compound (XVII') thus obtained is subjected to a cyclization reaction, optionally after removing the protecting group by virtue of a suitable method such as the action of an acid or a base, or catalytic reduction. This cyclization reaction is conducted by treating the compound (XVII') together with an organic acid such as methanesulfonic acid, an inorganic acid such as sulfuric acid or polyphosphoric acid or a mixture of such an organic or inorganic acid and phosphorus pentoxide at room temperature to 170° C., preferably at 80–120° C. In this case, a solvent which does not take part in the reaction may be added as needed.

As an alternative, the cyclization reaction can also be practiced by, optionally after addition of a catalyst, treating the compound (XVII') with oxalyl chloride, thionyl chloride, thionyl bromide, oxalyl bromide, phosgene, phosphorus trichloride, phosphorus tribromide, phosphoryl chloride, phosphoryl bromide or the like to convert it into its corresponding acid halide and then treating the acid halide at −20° C. to reflux temperature in the presence of a Lewis acid such as aluminum chloride, aluminum bromide, boron trifluoride-ether complex or tin tetrachloride in a solvent such as dichloromethane, 1,2-dichloroethane or nitromethane. In the above-described reactions, the compound (II) and the compound (II') can be formed at varied ratios by changing the reaction conditions.

Process 2

Among the pyrroloazepine compounds (I), compounds (Ia) and (Ia') in each of which $Z_1$ and $Z_2$ are combined together to represent an oxygen atom can be synthesized, for example, by any one of the following processes.

Process (a)

Each compound (Ia) or compound (Ia') can be obtained in accordance with the following reaction scheme, namely, by reacting a compound represented by the formula (II) or (II') with a compound represented by the formula (III) to convert the compound (II) or (II') into a compound represented by the formula (IV) or (IV') and then reacting a nitrogen-containing compound represented by the formula (V) or a salt thereof to the compound (IV) or (IV').

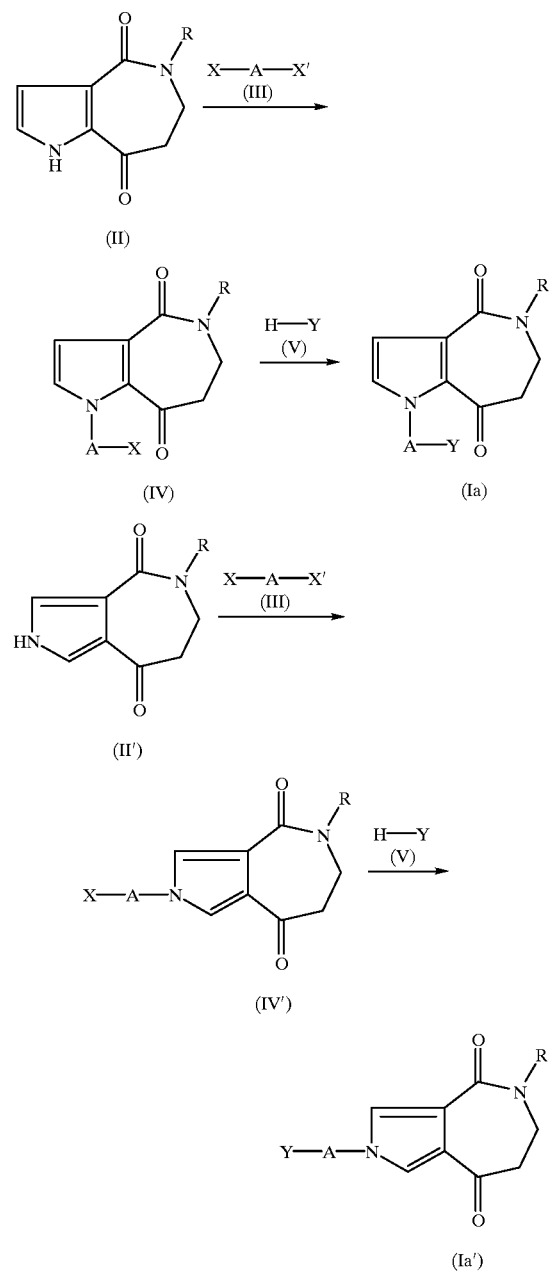

wherein A, R, X, X' and Y have the same meanings as defined above.

In the above-described reactions, the conversion from the compound (II) or (II') into the compound (IV) or (IV') can be effected by treating the compound (II) or (II') with an organic or inorganic base and then reacting the compound (III), or by causing the compound (III) to act on the compound (II) or (II') in the presence of such a base.

The groups X and X' in the compound (III) are eliminative groups. Illustrative can be halogen atoms such as chlorine and bromine, alkylsulfonyloxy groups such as methanesulfonyloxy, and arylsulfonyloxy groups such as p-toluenesulfonyloxy.

Exemplary organic or inorganic bases can include sodium carbonate, potassium carbonate, sodium hydroxide, potassium hydroxide, sodium hydride, triethylamine, sodium ethoxide, and potassium t-butoxide. Further, illustrative solvents usable in the above reaction can include acetone, 2-butanone, acetonitrile, dimethyl sulfoxide, dioxane and toluene. The reaction can be conducted at −20° C. to reflux temperature.

To prepare the compound (Ia) or (Ia') from the thus-obtained compound (IV) or (IV'), it is only necessary to react the compound (IV) or (IV') with the nitrogen-containing compound (V) or an organic acid salt or inorganic acid salt thereof in a solventless manner or in a solvent such as the above-described solvent, methanol or ethanol at room temperature to 150° C. In this reaction, an organic base such as triethylamine, pyridine, collidine or potassium t-butoxide or an inorganic base such as potassium carbonate, sodium carbonate, sodium hydrogencarbonate, sodium hydroxide or potassium hydroxide can be used as needed. Further, an alkali iodide such as potassium iodide or sodium iodide can also be added as needed.

Examples of the nitrogen-containing compound (V) can include 1-phenylpiperazine, 1-(2-fluorophenyl)-piperazine, 1-(3-fluorophenyl)piperazine, 1-(4-fluorophenyl)piperazine, 1-(4-hydroxyphenyl)piperazine, 1-(2-chlorophenyl)piperazine, 1-(3-chlorophenyl)piperazine, 1-(4-chlorophenyl)piperazine, 1-(2-methoxyphenyl)-piperazine, 1-(3-methoxyphenyl)piperazine, 1-(4-methoxyphenyl)piperazine, 1-(4-methanesulfonamidophenyl)piperazine, 1-(4-cyanophenyl)piperazine, 1-(4-carbamoylphenyl)piperazine, 1-(4-methoxycarbonyl-phenyl)piperazine, 1-(2-pyridyl)piperazine, 1-(2-pyrimidinyl)piperazine, 1-benzylpiperazine, 1-diphenyl-methylpiperazine, 1-cinnamylpiperazine, 1-benzoylpiperazine, 1-(4-benzyloxybenzoyl)piperazine, 1-(4-hydroxybenzoyl)piperazine, 1-(2-furoyl)piperazine, 1-(1,2-benzisoxazol-3-yl)piperazine, 1-(1,2-benzisothiazol-3-yl)piperazine, 4-phenylpiperidine, 4-benzylpiperidine, α,α-bis(4-fluorophenyl)-4-piperidinemethanol, 4-(4-fluorobenzoyl)piperidine, 4-benzoylpiperidine, 4-(4-methoxybenzoyl)piperidine, 4-(4-chlorobenzoyl)piperidine, 3-(4-fluorobenzoyl)-piperidine, 4-(6-fluoro-1,2-benzisoxazol-3-yl)-piperidine, 4-(6-fluoro-1,2-benzisothiazol-3-yl)-piperidine, 4-(6-fluoro-1H-indazol-3-yl)piperidine, 4-(4-fluorophenoxy)piperidine, 4-[(4-fluorophenyl)thio]-piperidine, 4-[(4-fluorophenyl)sulfinyl]piperidine, 4-[(4-fluorophenyl)sulfonyl]piperidine, 4-[bis(4-fluoro-phenyl)methylene]piperidine, and 4-(4-fluorobenzoyl)-piperidine ethylene acetal. They are either known or can be readily prepared by known processes or processes similar to such known processes.

Process (b)

Further, the compound (Ia) or (Ia') can be obtained by causing a compound represented by the formula (VI) to act on the compound represented by the formula (II) or (II') in accordance with the following reaction formula:

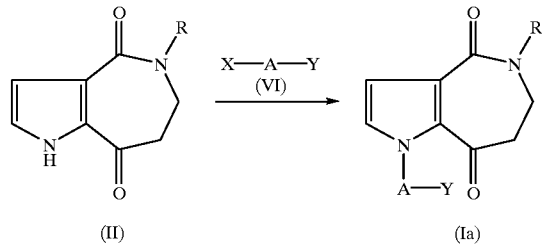

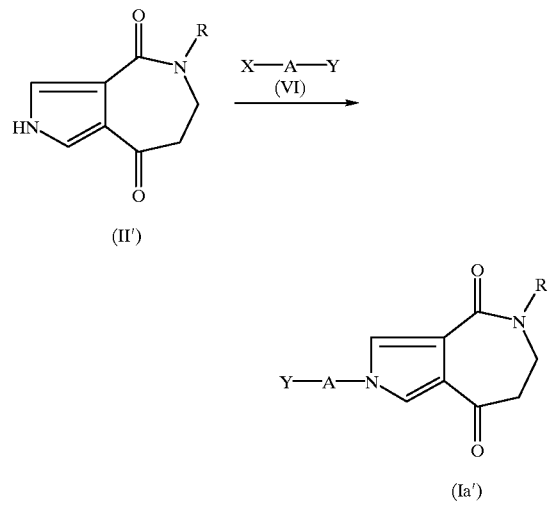

wherein A, R, X and Y have the same meanings as defined above.

The conversion from the compound (II) or (II') into the compound (Ia) or (Ia') is conducted by causing the compound (VI) to act either after treatment of the compound (II) or (II') with an inorganic base or an organic base or in the presence of an inorganic base or an organic base. Reaction conditions are similar to those employed upon conversion from the compound (II) into the compound (IV) and described above under Process (a) of Process 2. Further, the compound (VI) can be synthesized by reacting the compound (III) with the compound (V) in a manner known per se in the art.

Process 3

Among the pyrroloazepine compounds (I), the compounds (Ic), (Ic'), (If) and (If') in each of which $Z_1$ and $Z_2$ both represent groups $SR_5$ (in which $R_5$ has the same meaning as described above) or $Z_1$ and $Z_2$ are combined together to represent the group

wherein G has the same meaning as defined above can be synthesized by any one of the following processes.

Process (a)

The compound (If) or (If') is obtained in accordance with the following reaction scheme, namely, by reacting a thiol compound, which is represented by the formula (VIIa) or (VIIb) [the compound (VIIa) and the compound (VIIb) may hereinafter be collectively called "the thiol compound (VII)"], with a compound (II) or (II') and then causing a compound (VI) to act.

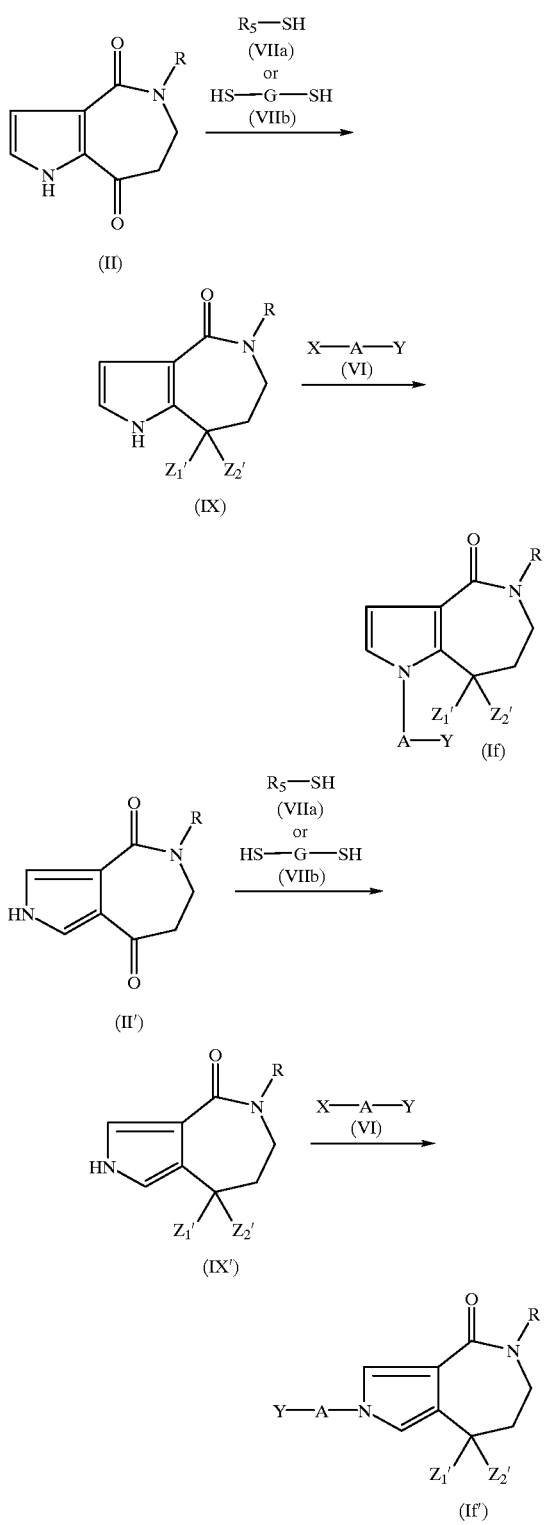

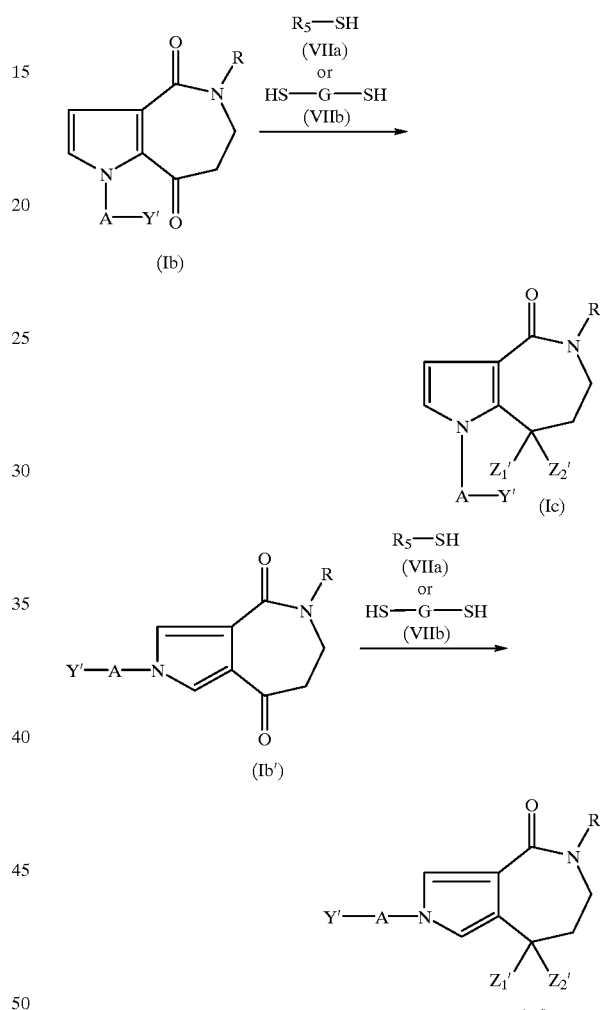

wherein A, G, R, $R_5$, X, Y, $Z_1'$ and $Z_2'$ have the same meanings as defined above.

For the conversion from the compound (II) or (II') into the compound (IX) or (IX'), a suitable method can be selected from those disclosed, for example, in T. W. Greene: "Protective Groups in Organic Synthesis" (John Wiley & Sons, Inc.) and the like. Describing one example, there is a process in which the thiol compound (VII) and boron trifluoride-ether complex are caused to act on the compound (II) or (II') in chloroform. Further, the conversion from the compound (IX) or (IX') into the compound (If) or (If') can be effected under the same conditions as in the conversion from the compound (II) into the compound (Ia) described above under Process (b) of Process 2.

Process (b)

Each compound represented by the formula (Ic) or (Ic') can be obtained by causing the thiol compound (VII) to act on a compound (Ib) or (Ib') in accordance with the following reaction scheme.

wherein A, G, R, $R_5$, Y' $Z_1'$ and $Z_2'$ have the same meanings as described above.

The conversion from the compound (Ib) or (Ib') into the compound (IC) or (Ic') can be effected under similar conditions as in the conversion of from the compound (II) into the compound (IX) described above under Process (a) of Process 3.

Process 4

Among the pyrroloazepine compounds (I), the compounds (Id) and (Id') and the compounds (Ig) and (Ig') in each of which $Z_1$ and $Z_2$ are combined together to represent a group $NOR_6$ can each be synthesized by any one of the following processes.

Process (a)

Each compound (Ig) or (Ig') is obtained in accordance with the following reaction scheme, namely, by causing hydroxylamine or a derivative thereof (VIII) or a salt thereof to act on a compound represented by the formula (IV) or (IV') and then causing a nitrogen-containing compound (V) to act.

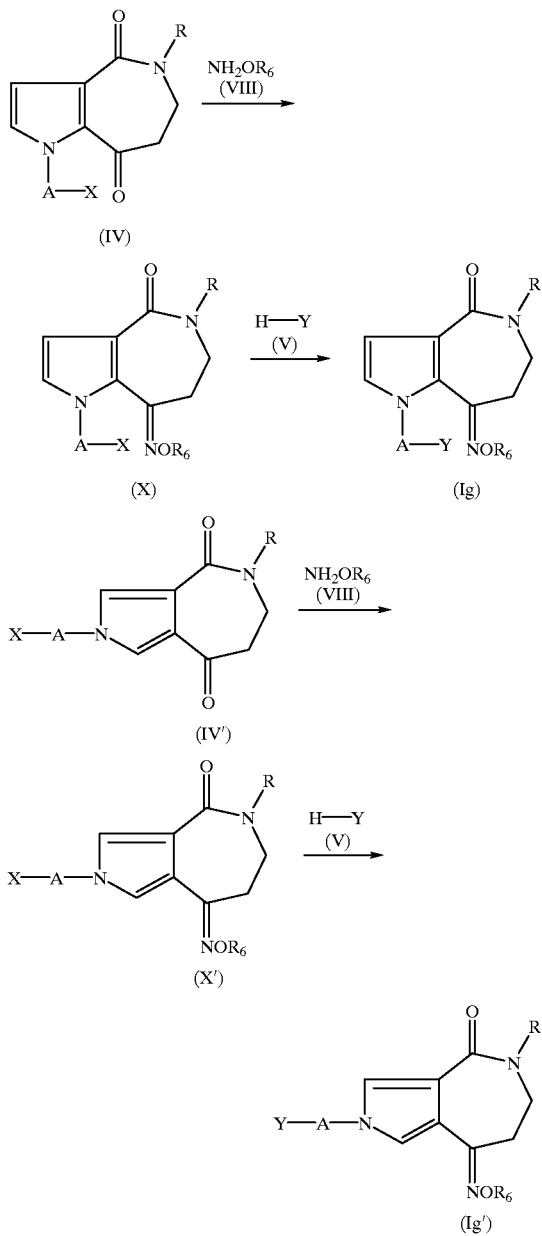

wherein A, R, $R_6$, X and Y have the same meanings as defined above.

The reaction between the compound (IV) or (IV') and the hydroxylamine or its derivative (VIII) is effected, if necessary, in the presence of an organic base such as pyridine, triethylamine, collidine or sodium acetate or an inorganic base such as potassium carbonate or sodium hydroxide. The hydroxylamine or its derivative (VIII) may also be used in the form of an organic acid salt or an inorganic acid salt.

The reaction is conducted at 0° C. to reflux temperature, preferably 0°C.–100° C. by adding a suitable solvent, for example, methanol, ethanol, propanol, tetrahydrofuran, dimethylformamide or dimethyl sulfoxide as needed.

Further, the conversion from the thus-obtained compound (X) or (X') into the compound (Ig) or (Ig') can be effected under similar conditions as in the conversion from the compound (IV) into the compound (Ia) shown above under Process (a) of Process 2.

Process (b)

Each compound (Id) or (Id') is obtained by causing hydroxylamine or its derivative (VIII) or a salt thereof to act on a compound (Ib) or (Ib') in accordance with the following reaction formula.

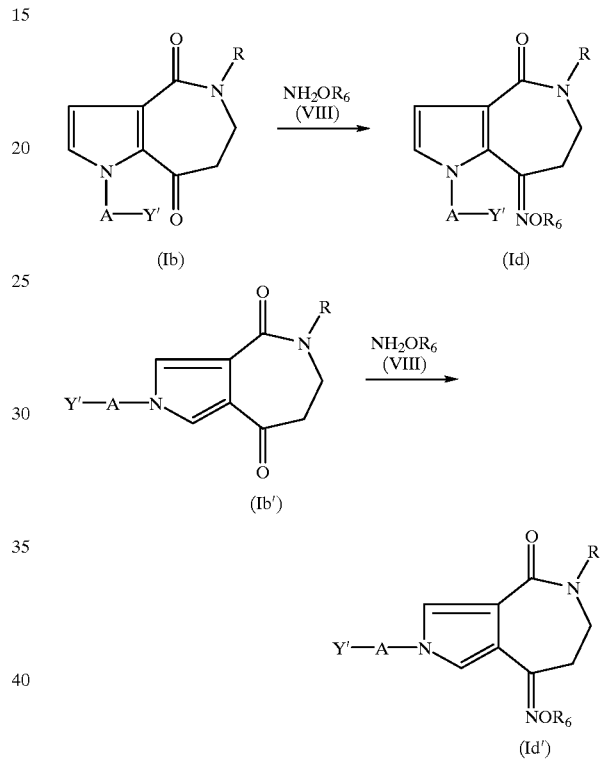

wherein A, R, $R_6$ and Y have the same meanings as defined above.

The conversion from the compound (Ib) or (Ib') into the compound (Id) or (Id') can be effected under similar conditions as the conversion from the compound (IV) into the compound (X) shown above under Process (a) of Process 4.

Process 5

Among the pyrroloazepine compounds (I), the compounds (Ie) and (Ie') and the compounds (Ih) and (Ih') in each of which $Z_1$ represents a hydrogen atom and $Z_2$ represents a hydroxyl group can each be synthesized by any one of the following processes.

Process (a)

Each compound (Ih) or (Ih') is obtained in accordance with the following reaction scheme, namely, by reducing a compound represented by the formula (IV) or (IV') and then causing a nitrogen-containing compound (V) to act.

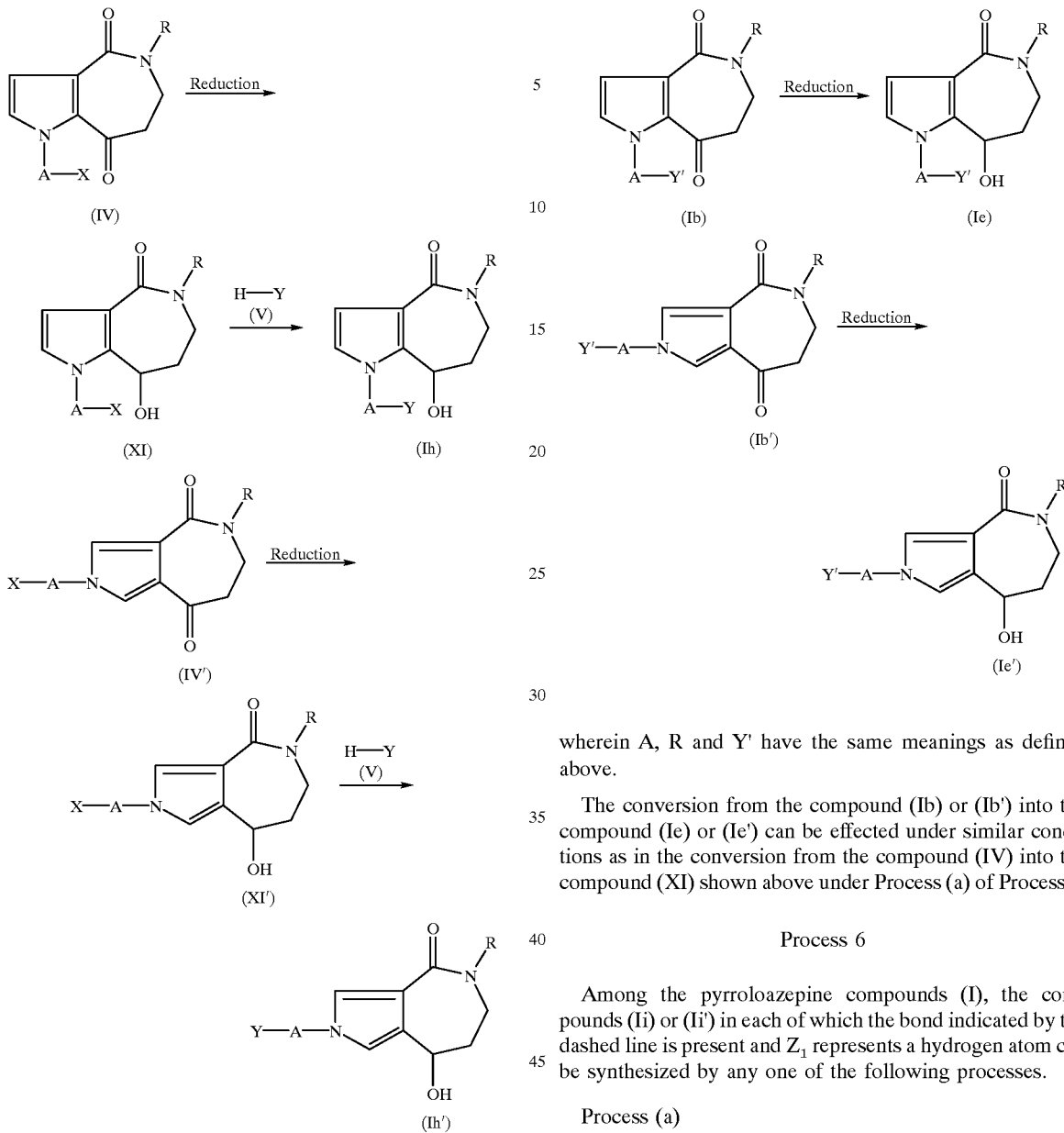

wherein A, R, X and Y have the same meanings as defined above.

The conversion from the compound (IV) or (IV') into the compound (XI) or (XII') is conducted by treating the compound (IV) or (IV') with a reducing agent such as sodium borohydride, potassium borohydride, sodium cyanoborohydride or tri(n-butyl)tin hydride at −78° C. to reflux temperature, preferably −20° C. to room temperature in an ordinarily-employed solvent.

The conversion from the compound (XI) or (XI') into the compound (Ih) or (Ih') can be effected under similar conditions as the conversion from the compound (IV) into the compound (Ia) shown above under Process (a) of Process 2.

Process (b)

Each compound (Ie) or (Ie') is obtained by reducing a compound represented by the formula (Ib) or (Ib') in accordance with the following reaction formula.

wherein A, R and Y' have the same meanings as defined above.

The conversion from the compound (Ib) or (Ib') into the compound (Ie) or (Ie') can be effected under similar conditions as in the conversion from the compound (IV) into the compound (XI) shown above under Process (a) of Process 5.

Process 6

Among the pyrroloazepine compounds (I), the compounds (Ii) or (Ii') in each of which the bond indicated by the dashed line is present and $Z_1$ represents a hydrogen atom can be synthesized by any one of the following processes.

Process (a)

Each compound (Ii) or (Ii') is obtained in accordance with the following reaction scheme, namely, by subjecting a compound represented by the formula (XI) or (XI') to a dehydrating reaction to obtain a compound represented by the formula (XII) or (XII') and then causing a nitrogen-containing compound (V) to act on the compound (XII) or (XII').

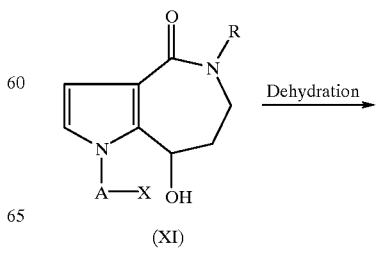

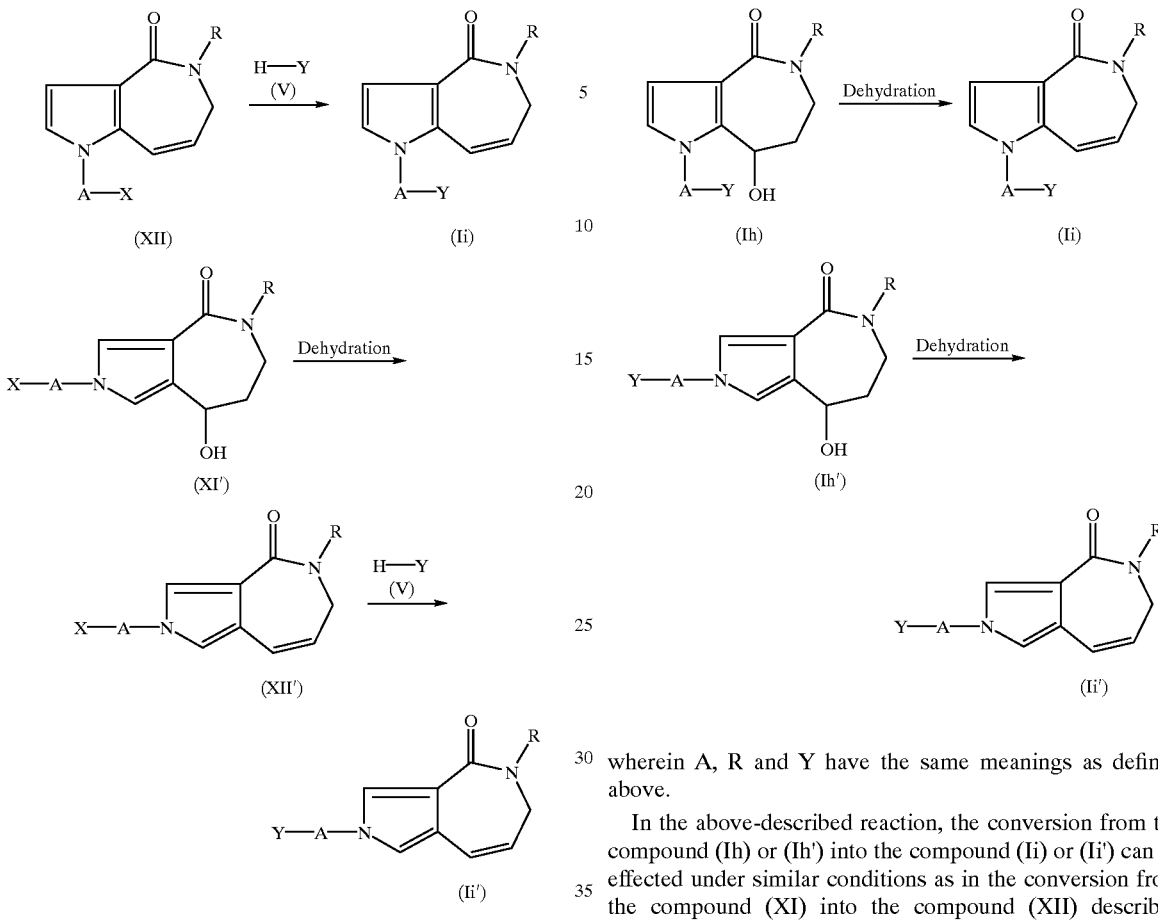

(XII)  (Ii)  (Ih)  (Ii)

(XI′)  (Ih′)

(XII′)  (Ii′)

(Ii′)

wherein A, R, X and Y have the same meanings as defined above.

In the above-described reaction, the conversion from the compound (XI) or (XI′) into the compound (XII) or (XII′) can be effected by treating the compound (XI) or (XI′) with an acid such as hydrogen chloride, hydrogen bromide, sulfuric acid, methanesulfonic acid or p-toluenesulfonic acid at −20° C. to 100° C., preferably at −20° C. to room temperature in a solvent such as water, methanol, ethanol, ethyl acetate, chloroform or toluene.

As an alternative, the conversion into the compound (XII) or (XII′) can also be effected by causing methanesulfonyl chloride, p-toluenesulfonyl chloride, phosphorus trichloride, phosphorus oxychloride, thionyl chloride or the like and a base such as triethylamine, pyridine or collidine to act on the compound (XI) or (XI′) in a solvent such as dichloromethane, chloroform or toluene.

The conversion from the compound (XII) or (XII′) into the compound (Ii) or (Ii′) can be effected under similar conditions as in the conversion from the compound (IV) into the compound (Ia) described above under Process (a) of Process 2.

Process (b)

Each compound (Ii) or (Ii′) is also obtained by subjecting a compound represented by the formula (Ih) or (Ih′) to a dehydrating reaction in accordance with the following reaction formula:

wherein A, R and Y have the same meanings as defined above.

In the above-described reaction, the conversion from the compound (Ih) or (Ih′) into the compound (Ii) or (Ii′) can be effected under similar conditions as in the conversion from the compound (XI) into the compound (XII) described above under Process (a) of Process 6.

Process 7

Among the pyrroloazepine compounds (I), compounds (Ij) or (Ij′) in each of which $Z_1$ and $Z_2$ both represent hydrogen atoms can be obtained in accordance with the following reaction scheme, namely, by reducing a compound represented by the formula (XII) or (XII′) to obtain a compound represented by the formula (XIII) or (XIII′) and then reacting a nitrogen-containing compound (V) to the compound (XIII) or (XIII′).

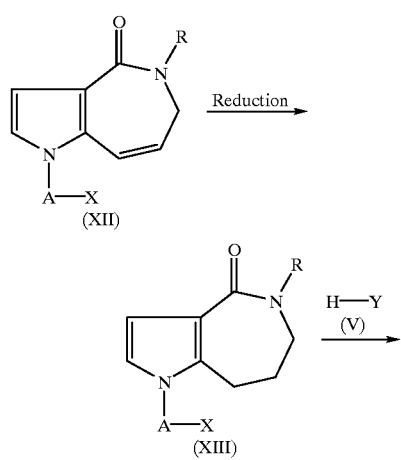

(XII)

(XIII)

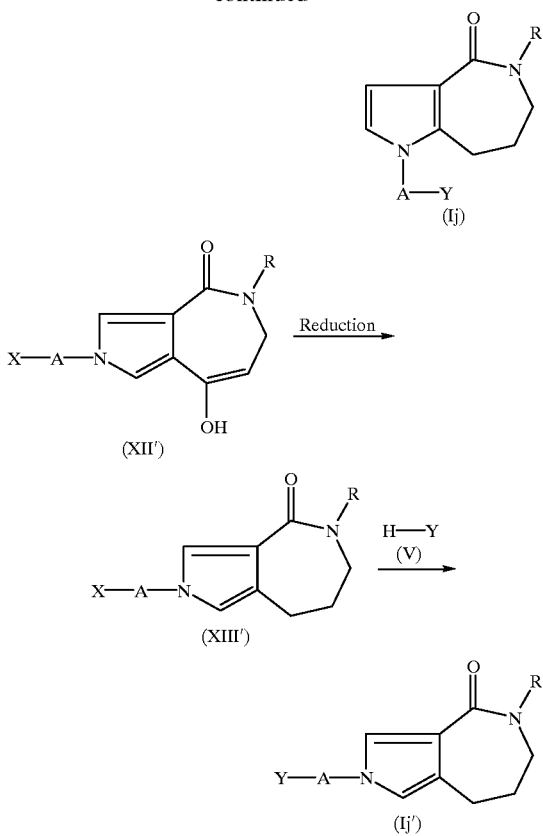

A, R, X and Y have the same meanings as defined above.

In the above-described reaction, the conversion from the compound (XII) or (XII') into the compound (XIII) or (XIII') can be conducted by treating, in the presence of a catalyst such as palladium-carbon or platinum, the compound (XII) or (XII') with hydrogen gas in an ordinarily-employed solvent at −78° C. to reflux temperature, preferably at room temperature. Further, the conversion from the compound (XIII) or (XIII') into the compound (Ij) or (Ij') can be effected under similar conditions as in the conversion from the compound (IV) into the compound (Ia) described above under Process (a) of Process 2.

If necessary, the compounds (I) of the present invention obtained according to the above-described processes can each be reacted with one of various acids to convert the compound into its salt. Then, the resulting salt can be purified by a method such as recrystallization or column chromatography.

Exemplary acids usable for the conversion of the pyrroloazepine compounds (I) into their salts can include inorganic acids such as hydrochloric acid, nitric acid, sulfuric acid, phosphoric acid and hydrobromic acid; and organic acids such as maleic acid, fumaric acid, tartaric acid, lactic acid, citric acid, acetic acid, methanesulfonic acid, p-toluenesulfonic acid, adipic acid, palmitic acid and tannic acid.

Further, the compounds (I) according to the present invention include many compounds containing asymmetric centers. Each racemic mixture can be resolved by one or more of various methods, whereby a single enantiomer can be obtained.

Usable methods include, for example:
(1) Resolution by an optical resolution column.
(2) Resolution by recrystallization subsequent to conversion into a salt with a chiral acid.
(3) Resolution by an enzyme reaction.
(4) Resolution by a combination of the above methods (1) to (3).

The pyrroloazepine compounds (I) and their salts, which are obtained as described above, have strong serotonin-2 blocking action and also $\alpha_1$ blocking action as will be demonstrated in tests to be described subsequently herein. From the results of a toxicity test, they have also been found to possess high safety. The compounds according to the present invention can therefore be used as pharmaceuticals for the treatment of circulatory diseases such as ischemic heart diseases, cerebrovascular disturbances, peripheral circulatory disturbances and hypertension.

When the pyrroloazepine compounds (I) according to this invention are used as pharmaceuticals, they can be administered in effective doses as they are. As an alternative, they can also be formulated into various preparation forms by known methods and then administered.

Exemplary preparation forms as pharmaceuticals include orally administrable preparation forms such as tablets, capsules and syrups as well as parenterally administrable preparation forms such as injections and suppositories. Whichever preparation form is used, a known liquid or solid extender or carrier usable for the formulation of the preparation form can be employed.

Examples of such extender or carrier include polyvinylpyrrolidone, arabic gum, gelatin, sorbit, cyclodextrin, tragacanth gum, magnesium stearate, talc, polyethylene glycol, polyvinyl alcohol, silica, lactose, crystalline cellulose, sugar, starch, calcium phosphate, vegetable oil, carboxymethylcellulose, sodium laurylsulfate, water, ethanol, glycerin, mannitol, syrup, and the like.

When the compounds (I) according to the present invention are used as pharmaceuticals, their dose varies depending on the administration purpose, the age, body weight, conditions, etc. of the patient to be administered. In oral administration, the daily dose may generally be about 0.01–1,000 mg.

The present invention will next be described in further detail by the following examples and tests. It is however to be noted that the present invention is by no means limited to the following examples and tests.

EXAMPLE 1

Synthesis of benzyl 3-(3-pyrrolecarboxamido)-propionate (Compound No. 1)

Into a solution of 1.67 g (15 mmol) of 3-pyrrolecarboxylic acid and 6.33 g (18 mmol) of β-alanine benzyl ester p-toluenesulfonate in 20 ml of dimethylformamide, a solution of 2.94 g (18 mmol) of diethyl phosphorocyanidate in 10 ml of dimethylformamide was added dropwise under ice cooling and stirring. A solution of 3.64 g (36 mmol) of triethylamine in 20 ml of dimethylformamide was then added dropwise. The reaction mixture was stirred at 0° C. for 1 hour and then at room temperature for 24 hours.

The reaction mixture was concentrated under reduced pressure, followed by the addition of a 3:1 mixed solvent of ethyl acetate and benzene to the residue. The resultant solution was washed successively with a half-saturated aqueous solution of potassium carbonate, water, a 10% aqueous solution of citric acid, water and a saturated aqueous solution of sodium chloride. The solution was dried over anhydrous sodium sulfate and was then concentrated under reduced pressure. The residue was purified by chromatography on a silica gel column ("Merck No. 9385" was used as its silica gel; the same silica gel was employed in the subsequent examples unless otherwise specifically indicated) (eluent: ethyl acetate/hexane=2:1), whereby 3.62 g of the title compound were obtained (yield: 89%).

EXAMPLE 2

Synthesis of ethyl N-methyl-3-(3-pyrrolecarboxamido) propionate (Compound No. 2)

Into a suspension of 3.30 g (30 mmol) of 3-pyrrolecarboxylic acid in 10 ml of dichloromethane, a solution of 5.90 g (45 mmol) of ethyl N-methyl-3-aminopropionate in 50 mt of dichloromethane, a solution of 4.55 g (45 mmol) of triethylamine in 50 ml of dichloromethane, and 8.63 g (45 mmol) of 1-ethyl-3-(3-dimethylaminopropyl)carbodiimide hydrochloride were successively added, followed by stirring at room temperature for 3 hours. Dichloromethane was added to the reaction mixture, and the resulting organic layer was washed successively with a 10% aqueous solution of citric acid, a saturated aqueous solution of sodium hydrogencarbonate and a saturated aqueous solution of sodium chloride. The organic layer was dried over anhydrous magnesium sulfate and was then concentrated under reduced pressure, whereby 5.31 g of the title compound were obtained (yield: 79%).

EXAMPLE 3

Synthesis of 3-(3-pyrrolecarboxamido)propionic acid (Compound No. 3)

Into a solution of 8.29 g (30.4 mmol) of Compound No. 1 in 200 ml of tetrahydrofuran, 829 mg of 5%-palladium-carbon were added, followed by stirring for 63 hours under a hydrogen gas stream. The reaction mixture was filtered and the thus-obtained solid matter was washed with methanol. The filtrate and the washing were combined and concentrated under reduced pressure. The residue was recrystallized from methanol-diisopropyl ether, whereby 3.89 g of the title compound were obtained (yield: 70%).

EXAMPLE 4

Synthesis of N-methyl-3-(3-pyrrolecarboxamido)-propionic acid (Compound No. 4)

A 2 N aqueous solution of sodium hydroxide (58 ml, 116 mmol) was added to 5.16 g (23 mmol) of Compound No. 2, followed by stirring at room temperature for 1.5 hours. After the reaction mixture was washed twice with ethyl ether, 6 N hydrochloric acid was added under ice cooling to adjust the pH of the mixture to 2. The mixture was saturated with sodium chloride. The resultant mixture was extracted four times with ethyl acetate. The extracts were combined, dried over anhydrous sodium sulfate, and then concentrated under reduced pressure. The thus-obtained crude crystals were recrystallized from ethyl acetatehexane, whereby 4.10 g of the title compound were obtained (yield: 91%).

EXAMPLE 5

Synthesis of 1,4,5,6,7,8-hexahydropyrrolo[3,2-c]azepine-4,8-dione (Compound No. 5) and 2,4,5,6,7,8-hexahydropyrrolo[3,4-c]azepine-4,8-dione (Compound No. 6)

A mixture of 310 mg (1.7 mmol) of Compound No. 3 and 15.5 g of polyphosphoric acid (80%) was stirred for 1 hour in an oil bath of 100° C. The reaction mixture was poured into 100 g of ice water, to which a 4 N aqueous solution of sodium hydroxide was added to adjust its pH to 6. The mixture was saturated with sodium chloride, followed by extraction (4 times) with tetrahydrofuran. The organic layer was washed with a saturated aqueous solution of sodium chloride, dried over anhydrous sodium sulfate, and then concentrated under reduced pressure. The residue was fractionated and purified by chromatography on a silica gel (eluent: methanol/chloroform=1/19→1/9), whereby 166 mg of Compound No. 5 and 73 mg of Compound No. 6 were obtained (yields: 59% and 26%).

EXAMPLE 6

Synthesis of 5-methyl-1,4,5,6,7,8-hexahydropyrrolo-[3,2-c]azepine-4,8-dione (Compound No. 7) and 5-methyl-2,4,5,6,7,8-hexahydropyrrolo[3,4-c]azepine-4,8-dione (Compound No. 8)

A mixture of 981 mg (5 mmol) of Compound No. 4 and 50 g of polyphosphoric acid (80%) was stirred for 30 minutes in an oil bath of 100° C. The reaction mixture was poured into 200 g of ice water, to which a 4 N aqueous solution of sodium hydroxide was added to adjust its pH to 5. The mixture was saturated with sodium chloride, followed by extraction (thrice) with tetrahydrofuran. The organic layer was washed with a saturated aqueous solution of sodium chloride, dried over anhydrous sodium sulfate, and then concentrated under reduced pressure. The residue was fractionated and purified by chromatography on a silica gel (eluent: methanol/chloroform=3/97), whereby 653 mg of Compound No. 7 and 178 mg of Compound No. 8 were obtained (yields: 73% and 20%).

EXAMPLE 7

Synthesis of 1-(4-chlorobutyl)-5-methyl-1,4,5,6,7,8-hexahydropyrrolo[3,2-c]azepine-4,8-dione (Compound No. 9)

A suspension of 3.03 g (17 mmol) of Compound No. 7, 9.40 g (68 mmol) of potassium carbonate and 11.66 g (68 mmol) of 1-bromo-4-chlorobutane in 100 ml of 2-butanone was refluxed for 11 hours. The reaction mixture was filtered, and the thus-obtained solid matter was washed with 2-butanone. The filtrate and the washing were combined and concentrated under reduced pressure. The residue was purified by chromatography on a silica gel column (eluent: methanol/chloroform=1/99), whereby 4.46 g of the title compound were obtained (yield: 98%).

EXAMPLE 8

Synthesis of 1-(4-bromobutyl)-5-methyl-1,4,5,6,7,8-hexahydropyrrolo[3,2-c]azepine-4,8-dione (Compound No. 10)

A suspension of 178 mg (1 mmol) of Compound No. 7, 691 mg (5 mmol) of potassium carbonate and 0.6 ml (5 mmol) of 1,4-dibromobutane in 20 ml of dimethylformamide was stirred for 1 hour in an oil bath of 80° C. The reaction mixture was concentrated under reduced pressure. Ice water was added to the residue, followed by neutralization with 6 N hydrochloric.acid. The thus-obtained mixture was extracted with chloroform (thrice). The organic layer was washed with a saturated aqueous solution of sodium chloride, dried over anhydrous sodium sulfate, and concentrated under reduced pressure. The residue was purified by chromatography on a silica gel column (eluent: ethyl acetate), whereby 254 mg of the title compound were obtained (yield: 81%).

EXAMPLE 9

Synthesis of 2-(4-chlorobutyl)-5-methyl-2,4,5,6,7,8-hexahydropyrrolo[3,4-c]azepine-4,8-dione (Compound No. 11)

A suspension of 891 mg (5 mmol) of Compound No. 8, 2.76 g (20 mmol) of potassium carbonate and 3.43 g (20 mmol) of 1-bromo-4-chlorobutane in 40 ml of 2-butanone was refluxed for 11 hours. The reaction mixture was post-treated in a similar manner as in Example 7 and the residue was purified by chromatography on a silica gel column (eluent: methanol/chloroform=1/49), whereby 1.29 g of the title compound were obtained (yield: 96%).

EXAMPLE 10

Synthesis of 1-(4-chlorobutyl)-8-hydroxyimino-5-methyl-1,4,5,6,7,8-hexahydropyrrolo[3,2-c]azepin-4-one (Compound No. 12)

A solution of 134 mg (0.5 mmol) of Compound No. 9 and 42 mg (0.6 mmol) of hydroxylamine hydrochloride in 10 ml of methanol was refluxed for 190 hours. The reaction mixture was concentrated under reduced pressure. A half-saturated aqueous solution of potassium carbonate was added to the residue, followed by extraction (twice) with chloroform. The organic layer was washed with a saturated aqueous solution of sodium chloride, dried over anhydrous sodium sulfate, and then concentrated under reduced pressure. The residue was purified by chromatography on a silica gel column (eluent: methanol/chloroform=1/99→1/49), whereby 70 mg of the title compound were obtained (yield: 49%).

EXAMPLE 11

Synthesis of 2-(4-chlorobutyl)-8-hydroxyimino-5-methyl-2,4,5,6,7,8-hexahydropyrrolo[3,4-c]azepin-4-one (Compound No. 13)

A solution of 537 mg (2 mmol) of Compound No. 11, 278 mg (4 mmol) of hydroxylamine hydrochloride and 328 mg (4 mmol) of sodium acetate in 20 ml of methanol was refluxed for 4 hours. The reaction mixture was post-treated in a similar manner as in Example 10 and the residue was purified by chromatography on a silica gel column (eluent: ethyl acetate), whereby 273 mg of the title compound were obtained (yield: 48%).

EXAMPLE 12

Synthesis of 1-(4-chlorobutyl)-8-hydroxy-5-methyl-1,4,5,6,7,8-hexahydropyrrolo[3,2-c]azepin-4-one (Compound No. 14)

Into a solution of 269 mg (1 mmol) of Compound No. 9 in 15 ml of ethanol, 378 mg (10 mmol) of sodium borohydride were added under ice cooling and stirring, followed by stirring at room temperature for 18 hours. Water (15 ml) was added to the reaction mixture. The resultant mixture was stirred at room temperature for 2 hours and then concentrated under reduced pressure. Water was added to the residue, followed by extraction (twice) with ethyl acetate. The organic layer was washed with a saturated aqueous solution of sodium chloride, dried over anhydrous sodium sulfate, and then concentrated under reduced pressure. The residue was purified by chromatography on a silica gel column (eluent: methanol/chloroform=1/49), whereby 246 mg of the title compound were obtained (yield: 91%).

EXAMPLE 13

Synthesis of 1-[4-[4-(4-fluorobenzoyl)piperidino]-butyl]-5-methyl-1,4,5,6,7,8-hexahydropyrrolo[3,2-c]azepine-4,8-dione (Compound No. 15)

A suspension of 100 mg (0.32 mmol) of Compound No. 10, 364 mg (0.96 mmol) of 4-(4-fluorobenzoyl)-piperidine p-toluenesulfonate, 265 mg (1.92 mmol) of potassium carbonate and 54 mg (0.38 mmol) of sodium iodide in 20 ml of dimethylformamide was stirred for 15 hours in an oil bath of 80° C. Water was added to the reaction mixture, followed by extraction with a 3:1 mixed solvent of ethyl acetate and benzene. The organic layer was washed with water (twice) and a saturated aqueous solution of sodium chloride, dried over anhydrous sodium sulfate, and then concentrated under reduced pressure. The residue was purified by chromatography on a silica gel column (eluent: methanol/chloroform=1/19), whereby 123 mg of the title compound were obtained (yield: 88%).

EXAMPLE 14

Synthesis of 5-methyl-1-[4-(4-phenylpiperazin-1-yl) butyl]-1,4,5,6,7,8-hexahydropyrrolo[3,2-c]-azepine-4,8-dione (Compound No. 16)

A suspension of 269 mg (1 mmol) of Compound No. 9, 162 mg (1 mmol) of N-phenylpiperazine, 168 mg (2 mmol) of sodium hydrogencarbonate and 300 mg (2 mmol) of sodium iodide in 15 ml of acetonitrile was refluxed for 11 hours. The reaction mixture was post-treated in a similar manner as in Example 10 and the residue was purified by chromatography on a silica gel column (eluent: methanol/chloroform=1/49), whereby 360 mg of the title compound were obtained (yield: 91%).

EXAMPLE 15

Synthesis of 1-[4-[4-(6-fluoro-1,2-benzisoxazol-3-yl) piperidino]butyl]-5-methyl-1,4,5,6,7,8-hexahydropyrrolo[3,2-c]azepine-4,8-dione (Compound No. 17)

A suspension of 269 mg (1 mmol) of Compound No. 9, 220 mg (1 mmol) of 4-(6-fluoro-1,2-benzisoxazol-3-yl) piperidine, 168 mg (2 mmol) of sodium hydrogencarbonate and 300 mg (2 mmol) of sodium iodide in 15 ml of acetonitrile was refluxed for 20 hours. The reaction mixture was post-treated in a similar manner as in Example 10. The residue was purified by chromatography on a silica gel column (eluent: methanol/chloroform=3/97), whereby 406 mg of the title compound were obtained (yield: 90%).

EXAMPLE 16

Synthesis of 2-[4-[4-(4-fluorobenzoyl)piperidino]-butyl]-5-methyl-2,4,5,6,7,8-hexahydropyrrolo[3,4-c]azepine-4,8-dione (Compound No. 18)

A suspension of 134 mg (0.5 mmol) of Compound No. 11, 122 mg (0.5 mmol) of 4-(4-fluorobenzoyl)piperidine hydrochloride, 168 mg (2 mmol) of sodium hydrogencarbonate and 150 mg (1 mmol) of sodium iodide in 10 ml of acetonitrile was refluxed for 25 hours. The reaction mixture was post-treated in a similar manner as in Example 10 and the residue was purified by chromatography on a silica gel column (eluent: methanol/chloroform=3/97), whereby 186 mg of the title compound were obtained (yield: 85%).

EXAMPLE 17

Synthesis of 1-[4-[4-(4-fluorobenzoyl)piperidino]-butyl]-8-hydroxyimino-5-methyl-1,4,5,6,7,8-hexahydropyrrolo[3,2-c]azepin-4-one (Compound No. 19)

A suspension of 57 mg (0.2 mmol) of Compound No. 12, 54 mg (0.22 mmol) of 4-(4-fluorobenzoyl)piperidine hydrochloride, 74 mg (0.88 mmol) of sodium hydrogencarbonate and 66 mg (0.44 mmol) of sodium iodide in 10 ml of acetonitrile was refluxed for 40 hours. The reaction mixture was post-treated in a similar manner as in Example 10 and the residue was purified by chromatography on a silica gel column (eluent: methanol/chloroform=3/97→1/19), whereby 72 mg of the title compound were obtained (yield: 79%).

EXAMPLE 18

Synthesis of 8-hydroxyimino-5-methyl-1-[4-(4-phenylpiperazin-1-yl)butyl]-1,4,5,6,7,8-hexahydropyrrolo[3,2-c]azepin-4-one (Compound No. 20)

A solution of 70.4 mg (0.18 mmol) of Compound No. 16 and 29 mg (0.4 mmol) of hydroxylamine hydrochloride in 5 ml of pyridine was stirred for 77 hours in an oil bath of 70° C. The reaction mixture was post-treated in a similar manner as in Example 10 and the residue was purified by chromatography on a silica gel column (eluent: methanol/chloroform=3/97), whereby 47 mg of the title compound were obtained (yield: 64%).

EXAMPLE 19

Synthesis of 2-[4-[4-(4-fluorobenzoyl)piperidino]-butyl]-8-hydroxyimino-5-methyl-2,4,5,6,7,8-hexahydropyrrolo[3,4-c]azepin-4-one (Compound No. 21)

A suspension of 142 mg (0.5 mmol) of Compound No. 13, 122 mg (0.5 mmol) of 4-(4-fluorobenzoyl)piperidine hydrochloride, 168 mg (2 mmol) of sodium hydrogencarbonate and 150 mg (1 mmol) of sodium iodide in 10 ml of acetonitrile was refluxed for 22 hours. The reaction mixture was post-treated in a similar manner as in Example 10 and the residue was purified by chromatography on a silica gel column (eluent: methanol/chloroform=1/9), whereby 202 mg of the title compound were obtained (yield: 89%).

EXAMPLE 20

Synthesis of 1-[4-[4-(4-fluorobenzoyl)piperidino]-butyl]-8-hydroxy-5-methyl-1,4,5,6,7,8-hexahydropyrrolo[3,2-c]azepin-4-one (Compound No. 22)

A suspension of 217 mg (0.8 mmol) of Compound No. 14, 214 mg (0.88 mmol) of 4-(4-fluorobenzoyl)piperidine hydrochloride, 296 mg (3.52 mmol) of sodium hydrogen-carbonate and 264 mg (1.76 mmol) of sodium iodide in 15 ml of acetonitrile was refluxed for 24 hours. The reaction mixture was post-treated in a similar manner as in Example 10 and the residue was purified by chromatography on a silica gel column (eluent: methanol/chloroform=1/19→2/23), whereby 295 mg of the title compound were obtained (yield: 84%).

In the same manner or a similar manner as in any of the Examples described above, the following compounds are obtained.

(1) 1-[3-[4-(4-Fluorobenzoyl)piperidino]propyl]-5-methyl-1,4,5,6,7,8-hexahydropyrrolo[3,2-c]-azepine-4,8-dione (2) 1-[5-[4-(4-Fluorobenzoyl)piperidino]pentyl]-5-5methyl-1,4,5,6,7,8-hexahydropyrrolo[3,2-c]-azepine-4,8-dione (3) 2-[3-[4-(4-Fluorobenzoyl)piperidino]propyl]-5-methyl-2,4,5,6,7,8-hexahydropyrrolo[3,4-c]-azepine-4,8-dione (4) 2-[5-[4-(4-Fluorobenzoyl)piperidino]pentyl]-5-methyl-2,4,5,6,7,8-hexahydropyrrolo[3,4-c]-azepine-4,8-dione (5) 1-[4-[4-(4-Fluorobenzoyl)piperidino]butyl]-1,4,5,6,7,8-hexahydropyrrolo[3,2-c]azepine-4,8-dione (6) 5-Ethyl-1-[4-[4-(4-fluorobenzoyl)piperidino]-butyl]-1,4,5,6,7,8-hexahydropyrrolo[3,2-c]-azepine-4,8-dione (7) 1-[4-[4-(4-Fluorobenzoyl)piperidino]butyl]-5-propyl-1,4,5,6,7,8-hexahydropyrrolo[3,2-c]-azepine-4,8-dione (8) 1-[4-[4-(4-Fluorobenzoyl)piperidino]butyl]-5-isopropyl-1,4,5,6,7,8-hexahydropyrrolo[3,2-c]-azepine-4,8-dione (9) 5-Butyl-1-[4-[4-(4-fluorobenzoyl)piperidino]-butyl]-1,4,5,6,7,8-hexahydropyrrolo[3,2-c]-azepine-4,8-dione

(10) 5-Benzyl-1-[4-[4-(4-fluorobenzoyl)piperidino]-butyl]-1,4,5,6,7,8-hexahydropyrrolo[3,2-c]-azepine-4,8-dione

(11) 1-[4-[4-(4-Fluorobenzoyl)piperidino]butyl]-5-methyl-1,4,5,6-tetrahydropyrrolo[3,2-c]azepin-4-one

(12) 1-[4-[4-(4-Fluorobenzoyl)piperidino]butyl]-5-methyl-1,4,5,6,7,8-hexahydropyrrolo[3,2-c]-azepin-4-one

(13) 8,8-Bis(ethylthio)-1-[4-[4-(4-fluorobenzoyl)-piperidino]butyl]-5-methyl-1,4,5,6,7,8-hexahydropyrrolo[3,2-c]azepin-4-one

(14) 1-[4-[4-(4-Fluorobenzoyl)piperidino]butyl]-5-methyl-1,4,5,6,7,8-hexahydropyrrolo[3,2-c]-azepin-4-one-8-spiro-2'-(1',3'-dithiolane)

(15) 1-[4-[4-(2-Furoyl)piperazin-1-yl]butyl]-5-methyl-1,4,5,6,7,8-hexahydropyrrolo[3,2-c]-azepine-4,8-dione

(16) 1-[4-[4-[Bis(4-fluorophenyl)methylene]-piperidino]butyl]-5-methyl-1,4,5,6,7,8-hexahydropyrrolo[3,2-c]azepine-4,8-dione

(17) 1-[4-[4-(6-Fluoro-1H-indazol-3-yl)piperidino]-butyl]-5-methyl-1,4,5,6,7,8-hexahydropyrrolo-[3,2-c]azepine-4,8-dione

(18) 1-[4-[4-(6-Fluoro-1,2-benzisothiazol-3-yl)-piperidino]butyl]-5-methyl-1,4,5,6,7,8-hexahydropyrrolo[3,2-c]azepine-4,8-dione

(19) 1-[4-[4-(4-Chlorobenzoyl)piperidino]butyl]-5-methyl-1,4,5,6,7,8-hexahydropyrrolo[3,2-c]-azepine-4,8-dione

(20) 1-[4-[4-(4-Fluorophenoxy)piperidino]butyl]-5-methyl-1,4,5,6,7,8-hexahydropyrrolo[3,2-c]-azepine-4,8-dione

(21) 1-[4-[4-(6-Fluoro-1,2-benzisoxazol-3-yl)-piperidino]butyl]-1,4,5,6,7,8-hexahydropyrrolo-[3,2-c]azepine-4,8-dione

(22) 5-Ethyl-1-[4-[4-(6-fluoro-1,2-benzisoxazol-3-yl)piperidino]butyl]-1,4,5,6,7,8-hexahydro-pyrrolo[3,2-c]azepine-4,8-dione

(23) 1-[4-[4-(6-Fluoro-1,2-benzisothiazol-3-yl)-piperidino]butyl]-1,4,5,6,7,8-hexahydropyrrolo-[3,2-c]azepine-4,8-dione

(24) 5-Ethyl-1-[4-[4-(6-fluoro-1,2-benzisothiazol-3-yl)piperidino]butyl]-1,4,5,6,7,8-hexahydropyrrolo[3,2-c]azepine-4,8-dione

(25) 2-[4-[4-(6-Fluoro-1,2-benzisoxazol-3-yl)-piperidino]butyl]-5-methyl-2,4,5,6,7,8-hexahydropyrrolo[3,4-c]azepine-4,8-dione Physical data of the compounds obtained above in Examples 1–20 are shown in Tables 1–6.

TABLE 1

| Comp'd No. | Structural formula | Property Melting point (recrystallization solvent) | NMR (δ ppm)* ( ): observation frequency | IR (cm$^{-1}$) ( ): measuring method |
|---|---|---|---|---|
| 1 | pyrrole-3-C(O)-NH-CH$_2$CH$_2$-COOBzl | Brown oil | (270 MHz) 2.64(2H, t, J=5.9Hz), 3.65(2H, m), 5.11(2H, s), 6.33(1H, m), 6.59(1H, m), 6.68(1H, m), 7.22(1H, m), 7.29–7.31(5H, m), 9.90(1H, br. s) | (film) 3271, 2954, 1732, 1634, 1567, 1520, 1338, 1254, 1210, 1172, 756, 698 |
| 2 | pyrrole-3-C(O)-N(Me)-CH$_2$CH$_2$-COOEt | Brown oil | (400 MHz) 1.26(3H, t, J=7.1Hz), 2.67(2H, t, J=7.1Hz), 3.18(3H, s), 3.81(2H, t, J=7.1Hz), 4.15(2H, q, J=7.1Hz), 6.44 (1H, m), 6.74(1H, m), 7.18(1H, m), 8.73(1H, br. s) | film) 3232, 2980, 1731, 1594, 1546, 1508, 1438, 1401, 1375, 1314, 1190, 1106, 1046, 968, 756 |
| 3 | pyrrole-3-C(O)-NH-CH$_2$CH$_2$-COOH | Colorless needle crystals 178.5–183.0° C. (methanol-isopropyl ether) | (400 MHz) (DMSO-d$_6$/TMS) 2.45(2H, t, J=7.1Hz), 3.36(2H, m), 6.43(1H, s), 6.71(1H, s), 7.26(1H, s), 7.72(1H, m), 11.04(1H, br. s), 12.09(1H, s) | (KBr) 3381, 3272, 1718, 1567, 1538, 1427, 1351, 1210, 853, 757 |
| 4 | pyrrole-3-C(O)-N(Me)-CH$_2$CH$_2$-COOH | Pale yellow powdery crystals 125.0–127.5° C. (ethyl acetate-hexane) | (400 MHz) (DMSO-d$_6$/TMS) 2.52(2H, m), 3.05(3H, s), 3.63 (2H, t, J=7.3Hz), 6.29(1H, m), 6.74 (1H, m), 7.12(1H, m), 11.11 (1H, br. s), 12.24(1H, br. s) | (KBr) 3330, 3122, 1721, 1574, 1516, 1407, 1305, 1211, 1098, 906, 752 |

*Measured in CDCl$_3$ with TMS as an internal standard unless otherwise specifically indicated.

TABLE 2

| Comp'd No. | Structural formula | Property Melting point (recrystallization solvent) | NMR (δ ppm)* ( ): observation frequency | IR (cm⁻¹) ( ): measuring method |
|---|---|---|---|---|
| 5 | | Colorless needle crystals 285–287° C. (decomp'd) (methanol-isopropyl ether) | (400 MHz)(DMSO-d₆/TMS) 2.71(2H, m) 3.33(2H, m), 6.57 (1H, s), 7.11(1H, d, J=2.4Hz), 8.29(1H, m), 12.13(1H, br. s) | (KBr) 3306, 3037, 2956, 1642, 1503, 1438, 1407, 1395, 1268, 882, 762 |
| 6 | | Colorless powdery crystals 287° C. min. (methanol-isopropyl ether) | (400 MHz) (DMSO-d₆/TMS) 2.65(2H, m), 3.29(2H, m), 7.34 (1H, s), 7.43(1H, s), 7.80 (1H, m), 11.97(1H, br. s) | (KBr) 3309, 3120, 3057, 2946, 2880, 1647, 1620, 1526, 1474, 1456, 1419, 1377, 1360, 910, 838, 810, 759 |
| 7 | | Colorless prism crystals 224.0–225.5° C. (chloroform-hexane) | (400 MHz) 2.86(2H, m), 3.23(3H, s), 3.71 (2H, m), 6.89(1H, t, J=2.8Hz), 7.04(1H, t, J=2.8Hz), 9.41 (1H, br. s) | (KBr) 3186, 1664, 1611, 1548, 1500, 1401, 1365, 1277, 1232, 1188, 1112, 1090, 955, 927, 890, 827, 785, 761, 692 |
| 8 | | Colorless prism crystals 175.0–176.5° C. (chloroform-hexane) | (400 MHz) 2.84(2H, m), 3.21(3H, s), 3.68 (2H, m), 7.41(1H, m), 7.47(1H, m), 10.32(1H, br. s) | (KBr) 3108, 2956, 1622, 1522, 1490, 1451, 1391, 1243, 1171, 1098, 958, 924, 863, 815, 758 |

*Measured in CDCl₃ with TMS as an internal standard unless otherwise specifically indicated.

TABLE 3

| Comp'd No. | Structural formula | Property Melting point (recrystallization solvent) | NMR (δ ppm)* ( ): observation frequency | IR (cm$^{-1}$) ( ): measuring method |
|---|---|---|---|---|
| 9 | (structure with Me-N, pyrrole, (CH$_2$)$_4$Cl) | Colorless needle crystals 88.0–89.0° C. (ethanol-isopropyl ether) | (270 MHz) 1.80(2H, m), 1.91(2H, m), 2.85(2H, m), 3.22(3H, s), 3.53(2H, t, J=6.6Hz), 3.66(2H, m), 4.35(2H, t, J=6.6Hz), 6.79(1H, d, J=2.6Hz), 6.89(1H, d, J=2.6Hz) | (KBr) 2937, 1630, 1522, 1504, 1410, 1318, 1246, 1178, 1095, 912, 862, 798, 750, 724 |
| 10 | (structure with Me-N, pyrrole, (CH$_2$)$_4$Br) | Colorless needle crystals 92.0–93.0° C. (ethyl acetate-hexane) | (270 MHz) 1.80–1.99(4H, m), 2.85(2H, m), 3.22(3H, s), 3.39(2H, t, J=5.9Hz), 3.66(2H, m), 4.34(2H, t, J=6.6Hz), 6.79(1H, d, J=2.6Hz), 6.89 (1H, d, J=2.6Hz) | (KBr) 3630, 2934, 1649, 1630, 1505, 1410, 1247, 1180, 1098, 911, 752 |
| 11 | (structure with Me-N, pyrrole, (CH$_2$)$_4$Cl) | Colorless powdery crystals 112.0–113.5° C. (chloroform-ether) | (400 MHz) 1.77(2H, m), 1.99(2H, m), 2.81(2H, m), 3.19(3H, s), 3.54(2H, t, J=6.3Hz), 3.66(2H, m), 3.96(2H, t, J=7.0Hz), 7.33(2H, m) | (KBr) 3116, 2948, 1655, 1624, 1540, 1519, 1490, 1406, 1318, 1244, 1169, 925, 879, 761 |
| 12 | (structure with Me-N, NOH, pyrrole, (CH$_2$)$_4$Cl) | Colorless prism crystals 194.0–195.5° C. (ethyl acetate-hexane) | (400 MHz) (DMSO-d$_6$/TMS) 1.63(2H, m), 1.78(2H, m), 2.89 (2H, m), 2.97(3H, s), 3.42(2H, m), 3.58(2H, t, J=6.6Hz), 4.19 (2H, t, J=6.9Hz), 6.36(1H, d, J=2.9Hz), 6.94(1H, d, J=2.9Hz) | (KBr) 3154, 2937, 1591, 1508, 1397, 1322, 1250, 1203, 1099, 1028, 972, 934, 916, 776, 741, 684 |

*Measured in CDCl$_3$ with TMS as an internal standard unless otherwise specifically indicated.

TABLE 4

| Comp'd No. | Structural formula | Property Melting point (recrystallization solvent) | NMR (δ ppm)* ( ): observation frequency | IR (cm⁻¹) ( ): measuring method |
|---|---|---|---|---|
| 13 | (structure: bicyclic pyrrole system with Me-N, C=O, =NOH, and N—(CH$_2$)$_4$Cl substituents) | Colorless prism crystals 184.0–186.0° C. (methanol) | (400 MHz) (DMSO-d$_6$/TMS) 1.66(2H, m), 1.84(2H, m), 2.78 (2H, m), 2.96(3H, s), 3.42(2H, m), 3.63(2H, t, J=6.6Hz), 3.96(2H, t, J=6.9Hz), 7.02(1H, d, J=2.5Hz), 7.27(1H, d, J=2.5Hz), 10.64(1H, s) | (KBr) 3230, 1598, 1530, 1408, 1360, 1325, 1247, 1186, 1144, 1044, 968, 950, 917, 836, 794, 679 |
| 14 | (structure: bicyclic pyrrole system with Me-N, C=O, OH, and N—(CH$_2$)$_4$Cl substituents) | Colorless prism crystals 106.5–111.5° C. (ethyl acetate-hexane) | (400 MHz) 1.82(2H, m), 1.98(2H, m), 2.23 (2H, m), 3.09(3H, s), 3.29(1H, m), 3.54(2H, dt, J=1.7Hz, 6.3Hz), 3.64(1H, m), 3.97(1H, m), 4.15 (1H, m), 4.91(1H, m), 6.66 (1H, d, J=2.9Hz), 6.72(1H, d, J=2.9Hz) | (KBr) 3251, 2930, 2871, 1593, 1545, 1512, 1466, 1390, 1316, 1292, 1258, 1211, 1102, 1057, 962, 722 |

TABLE 4-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 15 | 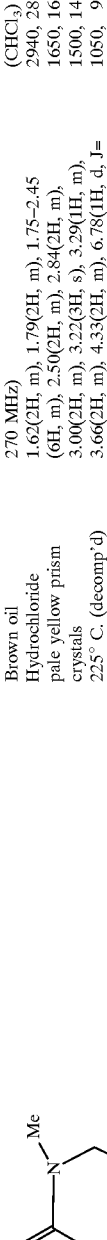 | Brown oil Hydrochloride pale yellow prism crystals 225° C. (decomp'd) (methanol-isopropyl ether) | (270 MHz) 1.62(2H, m), 1.79(2H, m), 1.75–2.45 (6H, m), 2.50(2H, m), 2.84(2H, m), 3.00(2H, m), 3.22(3H, s), 3.29(1H, m), 3.66(2H, m), 4.33(2H, m), 6.78(1H, d, J=2.6Hz), 6.91(1H, d, J=2.6Hz), 7.14 (2H, t, J=8.6Hz), 7.95(2H, dd, J=5.3Hz, 8.6Hz), | (CHCl₃) 2940, 2800, 1680, 1650, 1620, 1600, 1500, 1410, 1390, 1050, 975, 910 |
| 16 |  | Pale yellow prism crystals 93.0–95.0° C. (ethyl acetate-hexane) | (400 MHz) 1.55(2H, m), 1.80(2H, m), 2.40(2H, m), 2.58(4H, m), 2.84(2H, m), 3.19(4H, m), 3.21(3H, s), 3.65(2H, t, J=7.2Hz), 4.34(2H, t, J=7.2Hz), 6.78(1H, d, J=2.6Hz), 6.85 (1H, m), 6.88–6.95(3H, m), 7.26(2H, m) | (KBr) 3089, 2811, 1634, 1499, 1407, 1384, 1309, 1227, 1138, 926, 804, 758, 695 |

*Measured in CDCl₃ with TMS as an internal standard unless otherwise specifically indicated.

TABLE 5

| Comp'd No. | Structural formula | Property Melting point (recrystallization solvent) | NMR (δ ppm)* ( ): observation frequency | IR (cm⁻¹) ( ): measuring method |
|---|---|---|---|---|
| 17 | | Pale yellow powdery crystals 114.0–117.0° C. (2-propanol) | (400 MHz) 1.55(2H, m), 1.80(2H, m), 2.00–2.17 (6H, m), 2.40(2H, m), 2.85(2H, m), 2.98–3.12(3H, m), 3.22(3H, s), 3.65(2H, m), 4.34(2H, t, J=7.2Hz), 6.79(1H, d, J=2.6Hz), 6.91(1H, d J=2.6Hz), 7.05(1H, dt, J=2.1Hz, 8.9Hz), 7.23(1H, dd, J=2.1Hz, 8.5Hz), 7.69(1H, dd, J=5.1Hz, 8.7Hz) | (KBr) 3098, 2944, 1652, 1616, 1502, 1395, 1316, 1269, 1250, 1137, 960, 905, 830, 758 |
| 18 | | Colorless powdery crystals 173.5–175.5° C. (ethanol-ether) | (400 MHz) 1.49(2H, m), 1.75–1.90(6H, m), 2.07 (2H, m), 2.35(2H, m), 2.80(2H, m), 2.93(2H, m), 3.14–3.22(4H, m), 3.65(2H, m), 3.93(2H, t, J=7.1Hz), 7.13(2H, m), 7.33(2H, m), 7.95(2H, m) | (KBr) 3120, 2945, 1670, 1608, 1541, 1519, 1445, 1394, 1323, 1248, 1210, 1177, 1144, 972, 860, 762 |

TABLE 5-continued

| Comp'd No. | Structural formula | Property Melting point (recrystallization solvent) | NMR (δ ppm)* ( ): observation frequency | IR (cm⁻¹) ( ): measuring method |
|---|---|---|---|---|
| 19 | (structure: methylated pyrrole-fused azepinone with =NOH oxime and N-(CH₂)₄-piperidine-4-yl-(4-fluorobenzoyl) substituent) | Colorless oil | (400 MHz) 1.54(2H, m), 1.77(2H, m), 1.82–1.90 (4H, m), 2.14(2H, m), 2.39(2H, t, J=7.4Hz), 2.97(2H, m), 3.02(2H, m), 3.12(3H, s), 3.22(1H, quint, J=7.3Hz), 3.50(2H, m), 4.16(2H, t, J=7.2Hz), 6.65(1H, d, J=2.8Hz), 6.69(1H, d, J=2.8Hz), 7.13(2H, m), 7.95(2H, m) | (KBr) 2945, 1680, 1598, 1505, 1397, 1244, 1209, 1158, 974, 937, 854, 736 |
| 20 | (structure: methylated pyrrole-fused azepinone with =NOH oxime and N-(CH₂)₄-(4-phenylpiperazin-1-yl) substituent) | Colorless prism crystals 200.0–203.0° C. (methanol-chloroform) | (270 MHz) 1.55(2H, m), 1.74(2H, m), 2.43(2H, m), 2.64(4H, m), 2.98(2H, m), 3.10(3H, s), 3.22(4H, m), 3.48(2H, m), 4.14(2H, m), 6.64(1H, d, J=2.6Hz), 6.67(1H, d, J=2.6Hz), 6.82–6.96(3H, m), 7.26(2H, m), 10.95(1H, br. s) | (CHCl₃) 3570, 2940, 2825, 1620, 1600, 1500, 1395, 1090, 970, 910 |

*Measured in CDCl₃ with TMS as an internal standard unless otherwise specifically indicated.

TABLE 6

| Comp'd No. | Structural formula | Property Melting point (recrystallization solvent) | NMR (δ ppm)* ( ): observation frequency | IR (cm⁻¹) ( ): measuring method |
|---|---|---|---|---|
| 21 | (structure with pyrrole fused azocinone bearing N-Me lactam, =NOH, and N-(CH₂)₄-piperidinyl-C(O)-4-fluorophenyl group) | Colorless powdery crystals 172.0–178.0° C. (chloroform) | (400 MHz) 1.51(2H, m), 1.75–1.90(6H, m), 2.07 (2H, m), 2.36(2H, m), 2.90–3.00(4H, m), 3.11(3H, s), 3.18(1H, m), 3.53(2H, m), 3.89(2H, t, J=7.1Hz), 6.95(1H, d, J= 2.5Hz), 7.13(2H, m), 7.27(1H, d, J= 2.5Hz), 7.84(1H, br. s), 7.95(2H, m) | (KBr) 2942, 1677, 1598, 1537, 1508, 1410, 1324, 1215, 1142, 1039, 969, 913, 856, 796 |
| 22 | (structure with N-Me azepinone fused pyrrole bearing =NOH and N-(CH₂)₄-piperidinyl-C(O)-4-fluorophenyl group) | Colorless prism crystals 173.0° C.–175.5° C. (chloroform-ether) | (400 MHz) 1.59(2H, m), 1.74–2.07(8H, m), 2.12–2.36(4H, m), 2.82(1H, m), 2.95(1H, m), 3.13(3H, s), 3.18(1H, m), 3.30(1H, m), 3.75(1H, m), 4.01(2H, t, J=7.4Hz), 4.92 (1H, t, J=4.4Hz), 6.63(1H, d, J=2.9Hz), 6.74(1H, d, J=2.9Hz), 7.13(2H, m), 7.94(2H, m), | (KBr) 3274, 2935, 2808, 1672, 1586, 1511, 1317, 1284, 1207, 1154, 1101, 1057, 973, 856, 740 |

*Measured in CDCl₃ with TMS as an internal standard unless otherwise specifically indicated.

Tests

With respect to the compounds of the present invention, their anti-$\alpha_1$ action and anti-serotonin (5-HT) action were investigated by the methods which will be described below. The results of some representative compounds are shown in Table 7.

(1) Anti-$\alpha_1$ action

The thoracic aorta of each Hartley male guinea pig (body weight: 300–500 g) was excised. A preparation cut in a helical form was suspended under 1 g load in a Magnus cylinder filled with the Tyrode solution which had been aerated with a gas mixture of 95% $O_2$ and 5% $CO_2$ and maintained at 37° C. Using an isometric transducer ("TB-612J", manufactured by Nihon Kohden Corporation) and a pressure preamplifier ("AP-620G", manufactured by Nihon Kohden Corporation), variations in tension were measured. The isometric tensions were recorded on a thermal pen-writing recorder ("WT-647G", manufactured by Nihon Kohden Corporation). Taking the tonic contraction induced by $10^{-5}$ M norepinephrine (NE) as 100%, the percent contractions upon addition of each test drug at $10^{-8}$ M and $10^{-7}$ M were determined as anti-$\alpha_1$ action.

(2) Anti-serotonin (5-HT) action

The superior mesenteric artery of each Hartley male guinea pig (body weight: 300–500 g) was excised. A preparation cut in a helical form was suspended under restomg tension of 0.3 g in a Magnus cylinder filled with the Tyrode solution which had been aerated with a gas mixture of 95% $O_2$ and 5% $CO_2$ and maintained at 37° C. Using an isometric transducer ("UL-10", manufactured by SHINKOH K.K.) and a pressure preamplifier ("DSA-605A", manufactured by SHINKOH K.K.), variations in tension were measured. The isometric tensions were recorded on a pen-writing recorder ("VP-6537A", manufactured by NATIONAL K.K.). Taking the contraction induced by $10^{-5}$ M serotonin (5-HT) as 100%, the percent contractions by $10^{-5}$ M 5-HT in the presence of each test drug at $10^{-8}$ M, $10^{-7}$ M and $10^{-6}$ M were determined as anti-5-HT action.

(3) Results

TABLE 7

| Comp'd No. | Anti $\alpha_1$ action (% of Control) | | Anti 5-HT action (% of Control) | | |
|---|---|---|---|---|---|
| | $10^{-8}$M | $10^{-7}$M | $10^{-8}$M | $10^{-7}$M | $10^{-6}$M |
| 15 | 59.9 | 35.4 | NT | 75.3 | 26.6 |
| 17 | 27.8 | 14.0 | 80.7 | 55.2 | 8.9 |
| 18 | 76.0 | 37.3 | NT | 81.7 | 25.3 |
| 21 | 69.7 | 36.9 | NT | 85.5 | 24.9 |

NT . . . Not tested.

Capability of Exploitation in Industry

The pyrroloazepine derivatives (I) and their salts according to the present invention have strong $\alpha_1$-blocking action and serotonin-2 blocking action, and also have high safety. Accordingly, the present invention has made it possible to provide preventives or therapeutics for general circulatory diseases such as hypertension, heart failure, ischemic heart diseases, cerebrovascular disturbances and peripheral circulatory disturbances.

What is claimed is:

1. A compound or a salt thereof represented by formula (I):

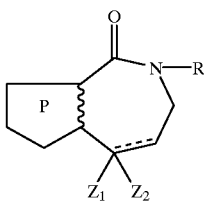

wherein the ring P is represented by the formula:

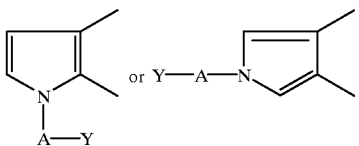

in which

A represents an alkylene group, an alkenylene group or an alkynylene group, and Y is a group represented by the formula:

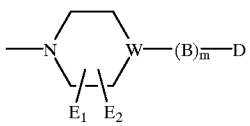

in which

W represents CH, C= or a nitrogen atom; and, when W represents CH, m is 0 or 1, B represents an oxygen atom, a sulfur atom, a carbonyl group, a sulfinyl group, a sulfonyl group, an alkylene group, an alkenylene group, a group —C(OH)R$_1$— in which R$_1$ represents a substituted or unsubstituted aryl group, wherein the substituents are selected from the group consisting of alkyl groups having 1–4 carbon atoms and aryl groups having 6–14 carbon atoms, wherein said alkyl and aryl groups may be substituted with one or more of halogen atoms, alkoxy groups having 1–4 carbon atoms, hydroxyl groups, cyano groups and nitro groups, a group —CHR$_2$— in which R$_2$ represents a substituted or unsubstituted aryl group, wherein said group may be substituted with one or more of halogen atoms, alkoxy groups having 1–4 carbon atoms, hydroxyl groups, cyano groups and nitro groups, or a substituted or unsubstituted, cyclic or acyclic acetal group, wherein said group may be substituted with one or more of halogen atoms, alkyl groups having 1–4 carbon atoms, aryl groups having from 6–14 carbon atoms, aralkyl groups having 7–22 carbon atoms and alkylidene groups having 1–4 carbon atoms;

when W represents C=, m is 1, B is a group represented by the formula:

in which the double bond is coupled with W and $R_3$ represents a substituted or unsubstituted aryl group or a substituted or unsubstituted aralkyl group, wherein the substituents are selected from the group consisting of one or more of halogen atoms, alkyl groups having 1–4 carbon atoms, alkoxy groups having 1–4 carbon atoms and hydroxyl groups;

when W represents a nitrogen atom, m is 0 or 1, and B represents a carbonyl group, a sulfonyl group, an alkylene group, an alkenylene group or a group —$CHR_4$— in which $R_4$ represents a substituted or unsubstituted aryl group, wherein said aryl group may be substituted with one or more of halogen atoms, alkyl groups having 1–4 carbon atoms and alkoxy groups having 1–4 carbon atoms;

$E_1$ and $E_2$ each independently represents a hydrogen atom or a lower alkyl group; and D represents a substituted or unsubstituted aromatic hydrocarbon group or a substituted or unsubstituted aromatic heterocyclic group, wherein said group may be substituted with one or more of halogen atoms, alkyl groups having 1–4 carbon atoms, alkoxy groups having 1–4 carbon atoms, aryl groups having 6–14 carbon atoms, aralkyl groups having 7–22 carbon atoms, aralkyloxy groups having 7–22 carbon atoms, cyano groups, nitro groups, carboxyl groups, alkoxycarbonyl groups, lower alkylsulfonylamino groups, carbamoyl groups and hydroxy groups;

the dashed line indicates the presence or absence of a bond; and, when the bond indicated by the dashed line is present, $Z_2$ is not present and $Z_1$ represents a hydrogen atom but, when the bond indicated by the dashed line is absent, $Z_1$ and $Z_2$ both represent hydrogen atoms; $Z_1$ represents a hydrogen atom and $Z_2$ represents a hydroxyl group; $Z_1$ and $Z_2$ both represent groups $SR_5$ in which $R_5$ represents a substituted or unsubstituted alkyl group, a substituted or unsubstituted aralkyl group or a substituted or unsubstituted aryl group, wherein said group may be substituted with one or more of halogen atoms, alkyl groups having 1–4 carbon atoms and alkoxy groups having 1–4 carbon atoms; $Z_1$ and $Z_2$ are combined together to represent an oxygen atom, a group $NOR_6$ in which $R_6$ represents a hydrogen atom, a substituted or unsubstituted alkyl group, a substituted or unsubstituted aralkyl group or a substituted or unsubstituted aryl group, wherein said group may be substituted with one or more of halogen atoms, alkyl groups having 1–4 carbon atoms and alkoxy groups having 1–4 carbon atoms, or a group represented by the formula:

in which

G represents a substituted or unsubstituted ethylene group or a substituted or unsubstituted trimethylene group, wherein said group may be substituted with one or more of halogen atoms, alkyl groups having 1–4 carbon atoms, aryl groups having 6–14 carbon atoms, aralkyl groups having 7–22 carbon atoms and alkylidene groups having 1–4 carbon atoms; and R represents a hydrogen atom, a linear or branched alkyl group, a cycloalkyl group, a cycloalkyl-alkyl group or a substituted or unsubstituted aralkyl group, wherein said aralkyl group may be substituted with one or more of halogen atoms, alkyl groups having 1–4 carbon atoms and alkoxy groups having 1–4 carbon atoms.

2. The compound or a salt thereof of claim 1, wherein $Z_1$ and $Z_2$ are combined together to represent an oxygen atom or the group $NOR_6$.

3. The compound or a salt thereof of claim 1, wherein $Z_1$ represents a hydrogen atom and $Z_2$ represents a hydroxyl group.

4. The compound or a salt thereof of claim 1, wherein A represents a tetramethylene group.

5. The compound or a salt thereof of claim 1, wherein W represents CH, B represents a carbonyl group, m is 1, and D represents said substituted or unsubstituted phenyl group.

6. The compound or a salt thereof of claim 1, wherein W represents CH, m is 0, and D represents said substituted or unsubstituted aromatic hydrocarbon group or said substituted or unsubstituted aromatic heterocyclic group.

7. The compound or a salt thereof of claim 1, wherein $E_1$ and $E_2$ each represent a hydrogen atom.

8. A process for the preparation of a compound represented by formula (Ia) or (Ia'):

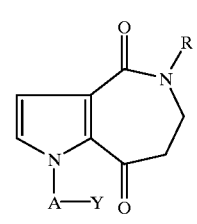

(Ia)

or

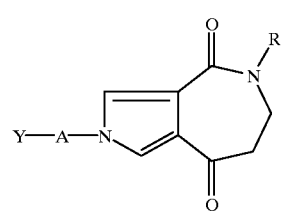

(Ia')

comprising:

reacting a compound is represented by formula (III):

X—A—X'  (III)

with a compound represented by formula (II) or (II'):

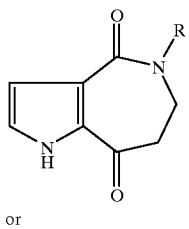
(II)

or

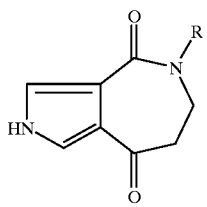
(II')

to produce a compound represented by formula (IV) or (IV'):

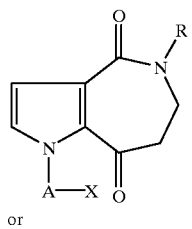
(IV)

or

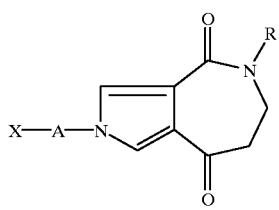
(IV')

and then
reacting a nitrogen-containing compound represented by formula (V):

H—Y (V)

with the compound represented by the formula (IV) or (IV'), wherein
A represents an alkylene group, an alkenylene group or an alkynylene group;
Y is a group represented by the formula:

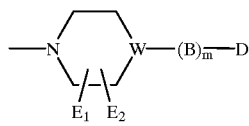

in which
W represents CH, C= or a nitrogen atom; and,
when W represents CH, m is 0 or 1, B represents an oxygen atom, a sulfur atom, a carbonyl group, a sulfinyl group, a sulfonyl group, an alkylene group, an alkenylene group, a group —C(OH)R$_1$— in which R$_1$ represents a substituted or unsubstituted aryl group, wherein the substituents are selected from the group consisting of alkyl groups having 1–4 carbon atoms and aryl groups having 6–14 carbon atoms, wherein said alkyl and aryl groups may be substituted with one or more of halogen atoms, alkoxy groups having 1–4 carbon atoms, hydroxyl groups, cyano groups and nitro groups, a group —CHR$_2$— in which R$_2$ represents a substituted or unsubstituted aryl group, wherein said aryl group may be substituted with one or more of halogen atoms, alkoxy groups having 1–4 carbon atoms, hydroxyl groups, cyano groups and nitro groups, or a substituted or unsubstituted, cyclic or acyclic acetal group, wherein said group may be substituted with one or more of halogen atoms, alkyl groups having 1–4 carbon atoms, aryl groups having from 6–14 carbon atoms, aralkyl groups having 7–22 carbon atoms and alkylidene groups having 1–4 carbon atoms;
when W represents C=, m is 1, B is a group represented by the formula:

in which the double bond is coupled with W and R$_3$ represents a substituted or unsubstituted aryl group or a substituted or unsubstituted aralkyl group, wherein the substituents are selected from the group consisting of one or more of halogen atoms, alkyl groups having 1–4 carbon atoms, alkoxy groups having 1–4 carbon atoms and hydroxyl groups;
when W represents a nitrogen atom, m is 0 or 1, and B represents a carbonyl group, a sulfonyl group, an alkylene group, an alkenylene group or a group —CHR$_4$— in which R$_4$ represents a substituted or unsubstituted aryl group, wherein said aryl group may be substituted with one or more of halogen atoms, alkyl groups having 1–4 carbon atoms and alkoxy groups having 1–4 carbon atoms;
E$_1$ and E$_2$ each independently represents a hydrogen atom or a lower alkyl group; and
D represents a substituted or unsubstituted aromatic hydrocarbon group or a substituted or unsubstituted aromatic heterocyclic group, wherein said group may be substituted with one or more of halogen atoms, alkyl groups having 1–4 carbon atoms, alkoxy groups having 1–4 carbon atoms, aryl groups having 6–14 carbon atoms, aralkyl groups having 7–22 carbon atoms, arakyloxy groups having 7–22 carbon atoms, cyano groups, nitro groups, carboxyl groups, alkoxycarbonyl groups, lower alkylsulfonylamino groups, carbamoyl groups and hydroxy groups;
R represents a hydrogen atom, a linear or branched alkyl group, a cycloalkyl group, a cycloalkyl-alkyl group or a substituted or unsubstituted aralkyl group, wherein said aralkyl group may be substituted with one or more of halogen atoms, alkyl groups having 1–4 carbon atoms and alkoxy groups having 1–4 carbon atoms; and
X and X' represent the same or different eliminative groups.

9. A process for the preparation of a compound represented by formula (Ia) or (Ia'):

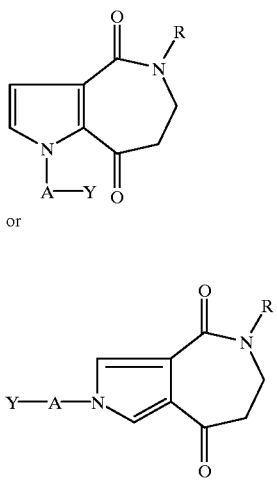
(Ia)

or (Ia')

comprising:
reacting a compound represented by formula (VI):

X—A—Y  (VI)

with a compound represented by the formula (II) or (II'):

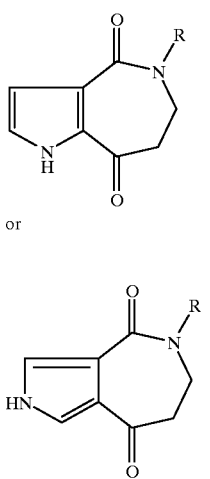
(II)

or (II')

wherein
A represents an alkylene group, an alkenylene group or an alkynylene group;
Y is a group represented by the formula:

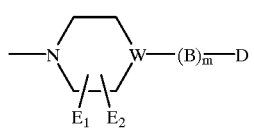

in which
W represents CH, C= or a nitrogen atom; and,
when W represents CH, m is 0 or 1, B represents an oxygen atom, a sulfur atom, a carbonyl group, a sulfinyl group, a sulfonyl group, an alkylene group, an alkenylene group, a group —C(OH)R— in which $R_1$ represents a substituted or unsubstituted aryl group, wherein the substituents are selected from the group consisting of alkyl groups having 1–4 carbon atoms and aryl groups having 6–14 carbon atoms, wherein said alkyl and aryl groups may be substituted with one or more of halogen atoms, alkoxy groups having 1–4 carbon atoms, hydroxyl groups, cyano groups or nitro groups, a group —$CHR_2$— in which $R_2$ represents a substituted or unsubstituted aryl group, wherein said aryl group may be substituted with one or more of halogen atoms, alkoxy groups having 1–4 carbon atoms, hydroxyl groups, cyano groups or nitro groups, or a substituted or unsubstituted, cyclic or acyclic acetal group, wherein said group maybe substituted with one or more of halogen atoms, alkyl groups having 1–4 carbon atoms, aryl groups having from 6–14 carbon atoms, aralkyl groups having 7–22 carbon atoms and alkylidene groups having 1–4 carbon atoms;

when W represents C=, m is 1, B is a group represented by the formula:

in which the double bond is coupled with W and $R_3$ represents a substituted or unsubstituted aryl group or a substituted or unsubstituted aralkyl group, wherein the substituents are selected from the group consisting of one or more of halogen atoms, alkyl groups having 1–4 carbon atoms, alkoxy groups having 1–4 carbon atoms and hydroxyl groups;

when W represents a nitrogen atom, m is 0 or 1, and B represents a carbonyl group, a sulfonyl group, an alkylene group, an alkenylene group or a group —$CHR_4$— in which $R_4$ represents a substituted or unsubstituted aryl group, wherein said aryl group may be substituted with one or more of halogen atoms, alkyl groups having 1–4 carbon atoms and alkoxy groups having 1–4 carbon atoms;

$E_1$ and $E_2$ each independently represents a hydrogen atom or a lower alkyl group; and D represents a substituted or unsubstituted aromatic hydrocarbon group or a substituted or unsubstituted aromatic heterocyclic group, wherein said group may be substituted with one or more of halogen atoms, alkyl groups having 1–4 carbon atoms, alkoxy groups having 1–4 carbon atoms, aryl groups having 6–14 carbon atoms, aralkyl groups having 7–22 carbon atoms, aralkyloxy groups having 7–22 carbon atoms, cyano groups, nitro groups, carboxyl groups, alkoxycarbonyl groups, lower alkylsulfonylamino groups, carbamoyl groups and hydroxy groups;

R represents a hydrogen atom, a linear or branched alkyl group, a cycloalkyl group, a cycloalkyl-alkyl group or a substituted or unsubstituted aralkyl group, wherein said aralkyl group may be substituted with one or more of halogen atoms, alkyl groups having 1–4 carbon atoms and alkoxy groups having 1–4 carbon atoms; and X and X' represent the same or different eliminative groups.

10. A process for the preparation of a compound represented by the formula (Ic) or (Ic'):

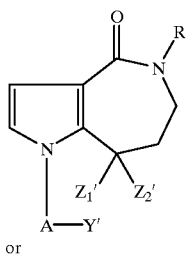

(Ic)

or

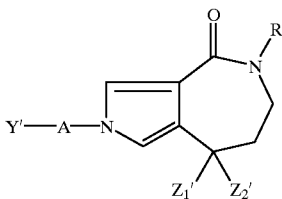

(Ic')

comprising:

reacting a compound represented by formula (Ib) or (Ib'):

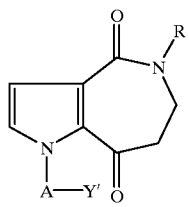

(Ib)

or

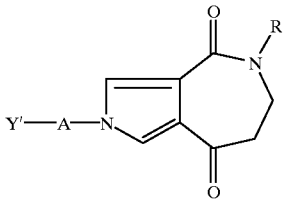

(Ib')

with a compound represented by the following formula (VIa) or (VIIB):

 (VIIa)

or

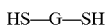 (VIIb)

wherein $Z_1'$ and $Z_2'$ both represent groups —$SR_5$, in which $R_5$ represents a substituted or unsubstituted alkyl group, a substituted or unsubstituted aralkyl group or a substituted or unsubstituted aryl group, wherein said group may be substituted with one or more of halogen atoms, alkyl groups having 1–4 carbon atoms and alkoxy groups having 1–4 carbon atoms or $Z_1'$ and $Z_2'$ are combined together to represent a group —S—G—S G in which G represents a substituted or unsubstituted ethylene group or a substituted or unsubstituted trimethylene group, wherein said group may be substituted with one or more of halogen atoms, alkyl groups having 1–4 carbon atoms, aryl groups having 6–14 carbon atoms, aralkyl groups having 7–22 carbon atoms and alkylidene groups having 1–4 carbon atoms, Y' represents a group

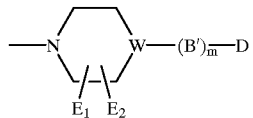

in which,

W represents CH, C= or a nitrogen atom; and when W represents CH, m is 0 or 1, B' represents an oxygen atom, a sulfur atom, a sulfinyl group, a sulfonyl group, an alkylene group, an alkenylene group, a group —C(OH)$R_1$— in which $R_1$ represents a substituted or unsubstituted aryl group, wherein the substituents are selected from the group consisting of alkyl groups having 1–4 carbon atoms and aryl groups having 6–14 carbon atoms, wherein said alkyl and aryl groups may be substituted with one or more of halogen atoms, alkoxy groups having 1–4 carbon atoms, hydroxyl groups, cyano groups and nitro groups, a group —CH$R_2$— in which $R_2$ represents a substituted or unsubstituted aryl group, wherein said aryl group may be substituted with one or more of halogen atoms, alkoxy groups having 1–4 carbon atoms, hydroxyl groups, cyano groups and nitro groups, or a substituted or unsubstituted, cyclic or acyclic acetal group, wherein said group may be substituted with one or more of halogen atoms, alkyl groups having 1–4 carbon atoms, aryl groups having from 6–14 carbon atoms, aralkyl groups having 7–22 carbon atoms and alkylidene groups having 1–4 carbon atoms;

when W represents C=, m is 1, B' represents a group

in which the double bond is coupled with W and $R_3$ represents a substituted or unsubstituted aryl group or a substituted or unsubstituted aralkyl group, wherein the substituents are selected from the group consisting of one or more of halogen atoms, alkyl groups having 1–4 carbon atoms, alkoxy groups having 1–4 carbon atoms and hydroxyl groups;

when W represents a nitrogen atom, m is 0 or 1, B' represents a carbonyl group, a sulfonyl group, an alkylene group, an alkenylene group or a group —CH$R_4$— in which $R_4$ represents a substituted or unsubstituted aryl group, wherein said aryl group may be substituted with one or more of halogen atoms, alkyl groups having 1–4 carbon atoms and alkoxy groups having 1–4 carbon atoms;

D represents a substituted or unsubstituted aromatic hydrocarbon group or a substituted or unsubstituted aromatic heterocyclic group, wherein said group may be substituted with one or more of halogen atoms, alkyl groups having 1–4 carbon atoms, alkoxy groups having 1–4 carbon atoms, aryl groups having 6–14 carbon atoms, aralkyl groups having 7–22 carbon atoms, aralkyloxy groups having 7–22 carbon atoms, cyano groups, nitro groups, carboxyl groups, alkoxycarbonyl groups, lower alkylsulfonylamino groups, carbamoyl groups and hydroxy groups;

$E_1$, $E_2$ each independently represent hydrogen atom or a lower alkyl group;

A represents an alkylene group, an alkenylene group or an alkynylene group;

R represents a hydrogen atom, a linear or branched alkyl group, a cycloalkyl group, a cycloalkyl-alkyl group or a substituted or unsubstituted aralkyl group, wherein said aralkyl group maybe substituted with one or more of halogen atoms, alkyl groups having 1–4 carbon atoms and alkoxy groups having 1–4 carbon atoms.

11. A process for the preparation of a compound represented by formula (Id) or (Id'):

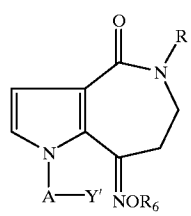

(Id)

or

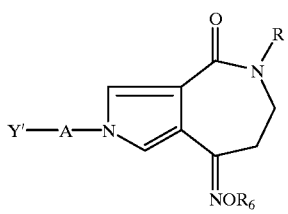

(Id')

comprising:
reacting a hydroxylamine or a derivative thereof represented by the following formula (VIII):

$NH_2OR_6$           (VIII)

with a pyrroloazepine compound represented by the following formula (Ib) or (Ib'):

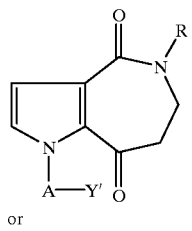

(Ib)

or

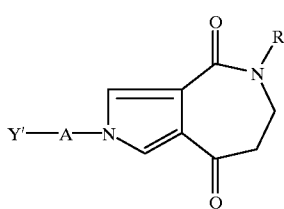

(Ib')

wherein
A represents an alkylene group, an alkenylene group or an alkynylene group;

Y' represents a group

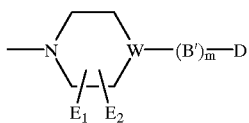

in which,
W represents CH, C= or a nitrogen atom; and
when W represents CH, m is 0 or 1, B' represents an oxygen atom, a sulfur atom, a sulfinyl group, a sulfonyl group, an alkylene group, an alkenylene group, a group —C(OH)$R_1$— in which $R_1$ represents a substituted or unsubstituted aryl group, wherein the substituents are selected from the group consisting of alkyl groups having 1–4 carbon atoms and aryl groups having 6–14 carbon atoms, wherein said alkyl and aryl groups may be substituted with one or more of halogen atoms, alkoxy groups having 1–4 carbon atoms, hydroxyl groups, cyano groups and nitro groups, a group —CHR$_2$— in which $R_2$ represents a substituted or unsubstituted aryl group, wherein said aryl group may be substituted with one or more of halogen atoms, alkoxy groups having 1–4 carbon atoms, hydroxyl groups, cyano groups and nitro groups, or a substituted or unsubstituted, cyclic or acyclic acetal group, wherein said group may be substituted with one or more of halogen atoms, alkyl groups having 1–4 carbon atoms, aryl groups having from 6–14 carbon atoms, aralkyl groups having 7–22 carbon atoms and alkylidene groups having 1–4 carbon atoms;

when W represents C=, m is 1, B' represents a group

in which the double bond is coupled with W and $R_3$ represents a substituted or unsubstituted aryl group or a substituted or unsubstituted aralkyl group, wherein the substituents are selected from the group consisting of one or more of halogen atoms, alkyl groups having 1–4 carbon atoms, alkoxy groups having 1–4 carbon atoms and hydroxyl groups;

when W represents a nitrogen atom, m is 0 or 1, B' represents a carbonyl group, a sulfonyl group, an alkylene group, an alkenylene group or a group —CHR$_4$— in which $R_4$ represents a substituted or unsubstituted aryl group, wherein said aryl group may be substituted with one or more of halogen atoms, alkyl groups having 1–4 carbon atoms and alkoxy groups having 1–4 carbon atoms;

$E_1$ and $E_2$ each independently represent a hydrogen atom or a lower alkyl group;

D represents a substituted or unsubstituted aromatic hydrocarbon group or a substituted or unsubstituted aromatic heterocyclic group, wherein said group may be substituted with one or more of halogen atoms, alkyl groups having 1–4 carbon atoms, alkoxy groups having 1–4 carbon atoms, aryl groups having 6–14 carbon atoms, aralkyl groups having 7–22 carbon atoms, aralkyloxy groups having 7–22 carbon atoms, cyano groups, nitro groups, carboxyl groups, alkoxycarbonyl groups, lower alkylsulfonylamino groups, carbamoyl groups and hydroxy groups;

R represents a hydrogen atom, a linear or branched alkyl group, a cycloalkyl group, a cycloalkyl-alkyl group or a substituted or unsubstituted aralkyl group, wherein said aralkyl group may be substituted with one or more of halogen atoms, alkyl groups having 1–4 carbon atoms and alkoxy groups having 1–4 carbon atoms;

$R_6$ represents a hydrogen atom, a substituted or unsubstituted alkyl group, a substituted or unsubstituted aralkyl group or a substituted or unsubstituted aryl group, wherein said group may be substituted with one or more of halogen atoms, alkyl groups having 1–4 carbon atoms and alkoxy groups having 1–4 carbon atoms.

12. A process for the preparation of a compound represented by formula (Ie) or (Ie'):

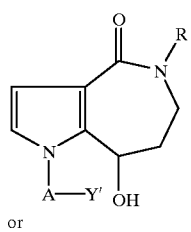

(Ie)

or

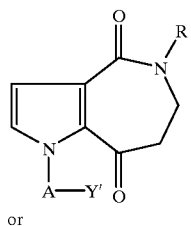

(Ie')

comprising:
reducing a compound represented by formula (Ib) or (Ib'):

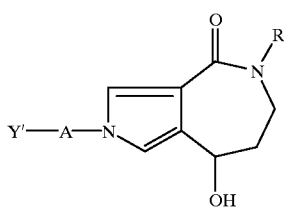

(Ib)

or

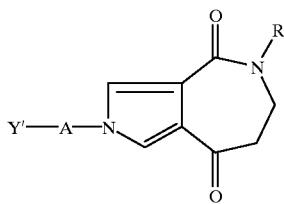

(Ib')

wherein
A represents an alkylene group, an alkenylene group or an alkynylene group,
R represents a hydrogen atom, a linear or branched alkyl group, a cycloalkyl group, a cycloalkyl-alkyl group or a substituted or unsubstituted aralkyl group, wherein said aralkyl group may be substituted with one or more of halogen atoms, alkyl groups having 1–4 carbon atoms and alkoxy groups having 1–4 carbon atoms, Y' represents a group

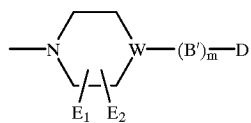

in which,
W represents CH, C= or a nitrogen atom; and
when W represents CH, m is 0 or 1, B' represents an oxygen atom, a sulfur atom, a sulfinyl group, a sulfonyl group, an alkylene group, an alkenylene group, a group —C(OH)$R_1$— in which $R_1$ represents a substituted or unsubstituted aryl group, wherein the substituents are selected from the group consisting of alkyl groups having 1–4 carbon atoms and aryl groups having 6–14 carbon atoms, wherein said alkyl and aryl groups may be substituted with one or more of halogen atoms, alkoxy groups having 1–4 carbon atoms, hydroxyl groups, cyano groups and nitro groups, a group —CHR$_2$— in which $R_2$ represents a substituted or unsubstituted aryl group, wherein said aryl group may be substituted with one or more of halogen atoms, alkoxy groups having 1–4 carbon atoms, hydroxyl groups, cyano groups and nitro groups, or a substituted or unsubstituted, cyclic or acyclic acetal group, wherein said group may be substituted with one or more of halogen atoms, alkyl groups having 1–4 carbon atoms, aryl groups having from 6–14 carbon atoms, aralkyl groups having 7–22 carbon atoms and alkylidene groups having 1–4 carbon atoms;

when W represents C=, m is 1, B' represents a group

in which the double bond is coupled with W and $R_3$ represents a substituted or unsubstituted aryl group or a substituted or unsubstituted aralkyl group, wherein the substituents are selected from the group consisting of one or more of halogen atoms, alkyl groups having 1–4 carbon atoms, alkoxy groups having 1–4 carbon atoms and hydroxyl groups;

when W represents a nitrogen atom, m is 0 or 1, B' represents a carbonyl group, a sulfonyl group, an alkylene group, an alkenylene group or a group —CHR$_4$— in which $R_4$ represents a substituted or unsubstituted aryl group, wherein said aryl group may be substituted with one or more of halogen atoms, alkyl groups having 1–4 carbon atoms and alkoxy groups having 1–4 carbon atoms;

$E_1$ and $E_2$ each independently represent a hydrogen atom or a lower alkyl group;

D represents a substituted or unsubstituted aromatic hydrocarbon group or a substituted or unsubstituted aromatic heterocyclic group, wherein said group may be substituted with one or more of halogen atoms, alkyl groups having 1–4 carbon atoms, alkoxy groups having 1–4 carbon atoms, aryl groups having 6–14 carbon atoms, aralkyl groups having 7–22 carbon atoms, aralkyloxy groups having 7–22 carbon atoms, cyano groups, nitro groups, carboxyl groups, alkoxycarbonyl groups, lower alkylsulfonylamino groups, carbamoyl groups and hydroxy groups.

13. A process for the preparation of a compound represented by the formula (If) or (If'):

(If)

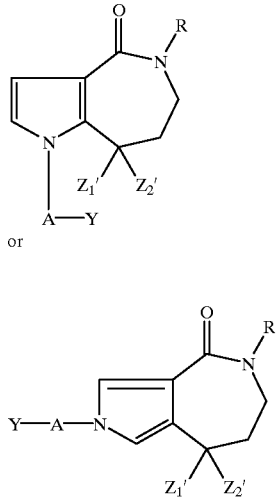

or (If')

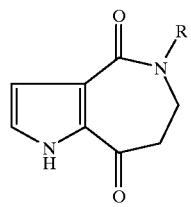

comprising:

reacting a compound represented by formula (VIIa) or (VIb):

 (VIIa)

or

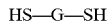 (VIIb)

with a compound represented by the following formula (II) or (II'):

(II)

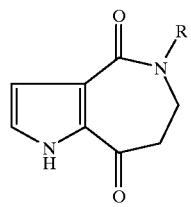

or (II')

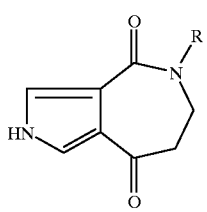

to produce a compound represented by formula (IX) or (IX'):

(IX)

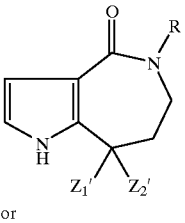

or (IX')

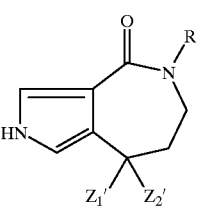

and then reacting a nitrogen-containing compound represented by formula (VI):

X—A—Y (VI)

with the compound represented by the formula (IX) or (IX'), wherein $Z_1'$ and $Z_2'$ both represent groups —$SR_5$, in which $R_5$ represents a substituted or unsubstituted alkyl group, a substituted or unsubstituted aralkyl group or a substituted or unsubstituted aryl group, wherein said group may be substituted with one or more of halogen atoms, alkyl groups having 1–4 carbon atoms and alkoxy groups having 1–4 carbon atoms or $Z_1'$ and $Z_2'$ are combined together to represent a group —S—G—S G in which G represents a substituted or unsubstituted ethylene group or a substituted or unsubstituted trimethylene group, wherein said group may be substituted with one or more of halogen atoms, alkyl groups having 1–4 carbon atoms, aryl groups having 6–14 carbon atoms, aralkyl groups having 7–22 carbon atoms and alkylidene groups having 1–4 carbon atoms;

A represents an alkylene group, an alkenylene group or an alkynylene group;

Y is a group represented by the formula:

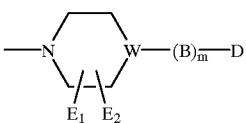

in which

W represents CH, C= or a nitrogen atom; and, when W represents CH, m is 0 or 1, B represents an oxygen atom, a sulfur atom, a carbonyl group, a sulfinyl group, a sulfonyl group, an alkylene group, an alkenylene group, a group —C(OH)$R_1$— in which $R_1$ represents a substituted or unsubstituted aryl group, wherein the substituents are selected from the group consisting of alkyl groups having 1–4 carbon atoms and aryl groups having 6–14 carbon atoms, wherein said alkyl and aryl groups may be substituted with one or more of halogen atoms, alkoxy groups having 1–4 carbon atoms, hydroxyl groups, cyano groups and nitro groups, a group —CHR$_2$— in which R$_2$ represents a substituted or unsubstituted aryl group, wherein said aryl group may be substituted with one or more of halogen atoms, alkoxy groups having 1–4 carbon atoms, hydroxyl groups, cyano groups or nitro groups, or a substituted or unsubstituted, cyclic or acyclic acetal group, wherein said group may be substituted with one or more of halogen atoms, alkyl groups having 1–4 carbon atoms, aryl groups having from 6–14 carbon atoms, aralkyl groups having 7–22 carbon atoms and alkylidene groups having 1–4 carbon atoms;

when W represents C=, m is 1, B is a group represented by the formula:

in which the double bond is coupled with W and R$_3$ represents a substituted or unsubstituted aryl group or a substituted or unsubstituted aralkyl group, wherein the substituents are selected from the group consisting of one or more of halogen atoms, alkyl groups having 1–4 carbon atoms, alkoxy groups having 1–4 carbon atoms and hydroxyl groups;

when W represents a nitrogen atom, m is 0 or 1, and B represents a carbonyl group, a sulfonyl group, an alkylene group, an alkenylene group or a group —CHR$_4$— in which R$_4$ represents a substituted or unsubstituted aryl group, wherein said aryl group may be substituted with one or more of halogen atoms, alkyl groups having 1–4 carbon atoms and alkoxy groups having 1–4 carbon atoms;

E$_1$ and E$_2$ each independently represents a hydrogen atom or a lower alkyl group;

D represents a substituted or unsubstituted aromatic hydrocarbon group or a substituted or unsubstituted aromatic heterocyclic group, wherein said group may be substituted with one or more of halogen atoms, alkyl groups having 1–4 carbon atoms, alkoxy groups having 1–4 carbon atoms, aryl groups having 6–14 carbon atoms, aralkyl groups having 7–22 carbon atoms, aralkyloxy groups having 7–22 carbon atoms, cyano groups, nitro groups, carboxyl groups, alkoxycarbonyl groups, lower alkylsulfonylamino groups, carbamoyl groups and hydroxy groups;

R represents a hydrogen atom, a linear or branched alkyl group, a cycloalkyl group, a cycloalkyl-alkyl group or a substituted or unsubstituted aralkyl group, wherein said aralkyl group may be substituted with one or more of halogen atoms, alkyl groups having 1–4 carbon atoms and alkoy groups having 1–4 carbon atoms; and X and X' represent the same or different eliminative groups.

14. A process for the preparation of a compound represented by formula (Ig) or (Ig'):

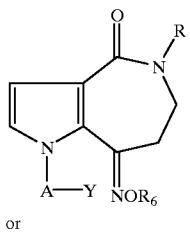
(Ig)

or

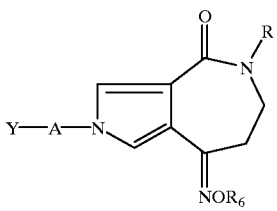
(Ig')

reacting a hydroxylamine or a derivative thereof represented by formula (VIII):

NH$_2$OR$_6$ (VIII)

with a compound represented by formula (IV) or (IV'):

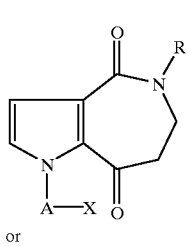
(IV)

or

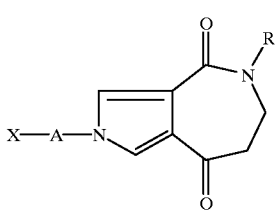
(IV')

to produce a compound represented by formula (X) or (X'):

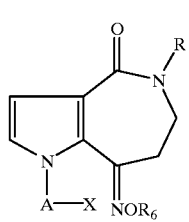
(X)

or

-continued (X')

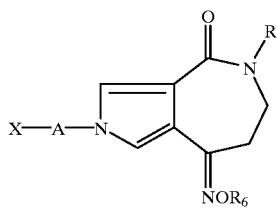

and then
reacting a nitrogen-containing compound represented by the formula (V):

H—Y  (V)

with the compound represented by the formula (X) or (X'), wherein
A represents an alkylene group, an alkenylene group or an alkynylene group;
Y is a group represented by the formula:

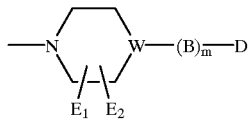

in which
W represents CH, C= or a nitrogen atom; and,
when W represents CH, m is 0 or 1, B represents an oxygen atom, a sulfur atom, a carbonyl group, a sulfinyl group, a sulfonyl group, an alkylene group, an alkenylene group, a group —C(OH)R$_1$— in which R$_1$ represents a substituted or unsubstituted aryl group, wherein the substituents are selected from the group consisting of alkyl groups having 1–4 carbon atoms and aryl groups having 6–14 carbon atoms, wherein said alkyl and aryl groups may be substituted with one or more of halogen atoms, alkoxy groups having 1–4 carbon atoms, hydroxyl groups, cyano groups or nitro groups, a group —CHR$_2$— in which R$_2$ represents a substituted or unsubstituted aryl group, wherein said aryl group may be substituted with one or more halogen atoms, alkoxy groups having 1—4 carbon atoms, hydroxyl groups, cyano groups and nitro groups, or a substituted or unsubstituted, cyclic or acyclic acetal group, wherein said group may be substituted with one or more of halogen atoms, alkyl groups having 1–4 carbon atoms, aryl groups having from 6–14 carbon atoms, aralkyl groups having 7–22 carbon atoms and alkylidene groups having 1–4 carbon atoms;
when W represents C=, m is 1, B is a group represented by the formula:

in which the double bond is coupled with W and R$_3$ represents a substituted or unsubstituted aryl group or a substituted or unsubstituted aralkyl group, wherein the substituents are selected from the group consisting of one or more of halogen atoms, alkyl groups having 1–4 carbon atoms, alkoxy groups having 1–4 carbon atoms and hydroxyl groups;

when W represents a nitrogen atom, m is 0 or 1, and B represents a carbonyl group, a sulfonyl group, an alkylene group, an alkenylene group or a group —CHR$_4$— in which R$_4$ represents a substituted or unsubstituted aryl group, wherein said aryl group may be substituted with one or more of halogen atoms, alkyl groups having 1–4 carbon atoms and alkoxy groups having 1–4 carbon atoms;

E$_1$ and E$_2$ each independently represents a hydrogen atom or a lower alkyl group;

D represents a substituted or unsubstituted aromatic hydrocarbon group or a substituted or unsubstituted aromatic heterocyclic group, wherein said group may be substituted with one or more of halogen atoms, alkyl groups having 1–4 carbon atoms, alkoxy groups having 1–4 carbon atoms, aryl groups having 6–14 carbon atoms, aralkyl groups having 7–22 carbon atoms, aralkyloxy groups having 7–22 carbon atoms, cyano groups, nitro groups, carboxyl groups, alkoxycarbonyl groups, lower alkylsulfonylamino groups, carbamoyl groups and hydroxy groups;

R represents a hydrogen atom, a linear or branched alkyl group, a cycloalkyl group, a cycloalkyl-alkyl group or a substituted or unsubstituted aralkyl group, wherein said aralkyl group may be substituted with one or more of halogen atoms, alkyl groups having 1–4 carbon atoms and alkoxy groups having 1–4 carbon atoms;

R$_6$ represents a hydrogen atom, a substituted or unsubstituted alkyl group, a substituted or unsubstituted aralkyl group or a substituted or unsubstituted aryl group, wherein said group may be substituted with one or more of halogen atoms, alkyl groups having 1–4 carbon atoms and alkoxy groups having 1–4 carbon atoms; and X and X' represent the same or different eliminative groups.

15. A process for the preparation of a compound represented by formula (Ih) or (Ih'):

(Ih)

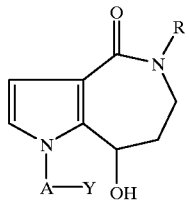

or (Ih')

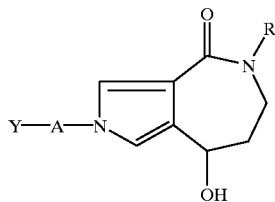

comprising:
reducing a compound represented by formula (IV) or (IV'):

(IV)

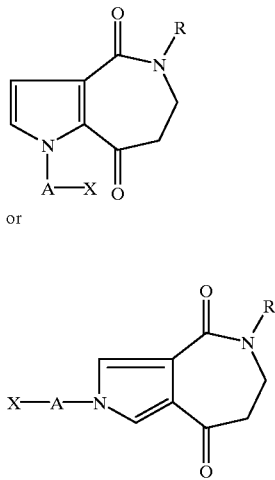

or (IV')

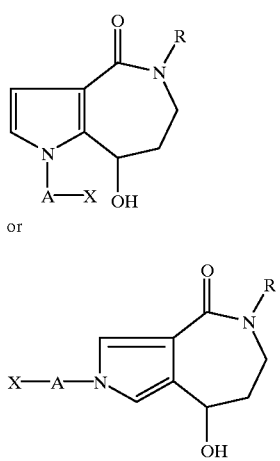

to produce a compound represented by formula (XI) or (XI'):

(XI)

or (XI')

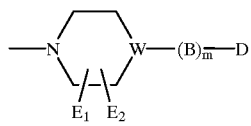

and then
reacting a nitrogen-containing compound represented by formula (IV):

H—Y                                (V)

with the compound represented by the formula (XI) or (XI'), wherein
A represents an alkylene group, an alkenylene group or an alkynylene group;
X is an eliminative group;
Y is a group represented by the formula:

in which
W represents CH, C= or a nitrogen atom; and,
when W represents CH, m is 0 or 1, B represents an oxygen atom, a sulfur atom, a carbonyl group, a sulfinyl group, a sulfonyl group, an alkylene group, an alkenylene group, a group —C(OH)R$_1$— in which R$_1$ represents a substituted or unsubstituted aryl group, wherein the substituents are selected from the group consisting of alkyl groups having 1–4 carbon atoms and aryl groups having 6–14 carbon atoms, wherein said alkyl and aryl groups may be substituted with one or more of halogen atoms, alkoxy groups having 1–4 carbon atoms, hydroxyl groups, cyano groups and nitro groups, a group —CHR$_2$— in which R$_2$ represents a substituted or unsubstituted aryl group, wherein said aryl group may be substituted with one or more of halogen atoms, alkoxy groups having 1–4 carbon atoms, hydroxyl groups, cyano groups and nitro groups, or a substituted or unsubstituted, cyclic or acyclic acetal group, wherein said group may be substituted with one or more of halogen atoms, alkyl groups having 1–4 carbon atoms, aryl groups having from 6–14 carbon atoms, aralkyl groups having 7–22 carbon atoms and alkylidene groups having 1–4 carbon atoms;

when W represents C=, m is 1, B is a group represented by the formula:

$$\underset{\diagup}{\overset{R_3}{=}}$$

in which the double bond is coupled with W and R$_3$ represents a substituted or unsubstituted aryl group or a substituted or unsubstituted aralkyl group, wherein the substituents are selected from the group consisting of one or more of halogen atoms, alkyl groups having 1–4 carbon atoms, alkoxy groups having 1–4 carbon atoms and hydroxyl groups;

when W represents a nitrogen atom, m is 0 or 1, and B represents a carbonyl group, a sulfonyl group, an alkylene group, an alkenylene group or a group —CHR$_4$— in which R$_4$ represents a substituted or unsubstituted aryl group, wherein said aryl group may be substituted with one or more of halogen atoms, alkyl groups having 1–4 carbon atoms and alkoxy groups having 1–4 carbon atoms;

E$_1$ and E$_2$ each independently represents a hydrogen atom or a lower alkyl group;

D represents a substituted or unsubstituted aromatic hydrocarbon group or a substituted or unsubstituted aromatic heterocyclic group, wherein said group may be substituted with one or more of halogen atoms, alkyl groups having 1–4 carbon atoms, alkoxy groups having 1–4 carbon atoms, aryl groups having 6–14 carbon atoms, aralkyl groups having 7–22 carbon atoms, aralkyloxy groups having 7–22 carbon atoms, cyano groups, nitro groups, carboxyl groups, alkoxycarbonyl groups, lower alkylsulfonylamino groups, carbamoyl groups and hydroxy groups; and R represents a hydrogen atom, a linear or branched alkyl group, a cycloalkyl group, a cycloalkyl-alkyl group or a substituted or unsubstituted aralkyl group, wherein said aralkyl group may be substituted with one or more of halogen atoms, alkyl groups having 1–4 carbon atoms and alkoxy groups having 1–4 carbon atoms.

16. A process for the preparation of a compound represented by formula (Ii) or (Ii'):

(Ii)

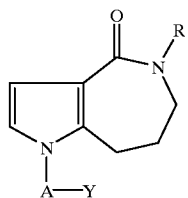

or (Ii')

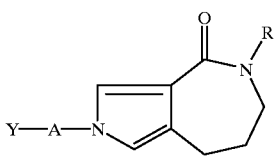

comprising:

dehydrating a compound represented by formula (XI) or (XI'):

(XI)

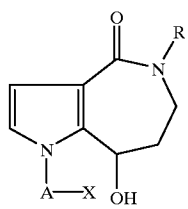

or (XI')

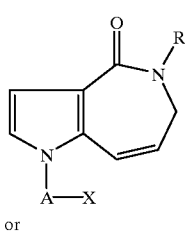

to produce a compound represented by formula (XII) or (XII'):

(XII)

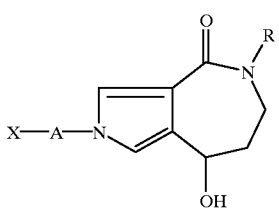

-continued (XII')

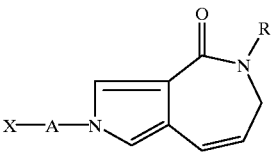

and then reacting a nitrogen-containing compound represented by formula (V):

$$H—Y \qquad (V)$$

with the compound represented by the formula (XII) or (XII'), wherein

A represents an alkylene group, an alkenylene group or an alkynylene group;

X is an eliminative group;

Y is a group represented by the formula:

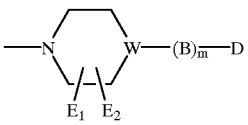

in which

W represents CH, C= or a nitrogen atom; and, when W represents CH, m is 0 or 1, B represents an oxygen atom, a sulfur atom, a carbonyl group, a sulfinyl group, a sulfonyl group, an alkylene group, an alkenylene group, a group —C(OH)$R_1$— in which $R_1$ represents a substituted or unsubstituted aryl group, wherein the substituents are selected from the group consisting of alkyl groups having 1–4 carbon atoms and aryl groups having 6–14 carbon atoms, wherein said alkyl and aryl groups may be substituted with one or more of halogen atoms, alkoxy groups having 1–4 carbon atoms, hydroxyl groups, cyano groups and nitro groups, a group —CH$R_2$— in which $R_2$ represents a substituted or unsubstituted aryl group, wherein said aryl group may be substituted with one or more of halogen atoms, alkoxy groups having 1–4 carbon atoms, hydroxyl groups, cyano groups and nitro groups, or a substituted or unsubstituted, cyclic or acyclic acetal group, wherein said group may be substituted with one or more of halogen atoms, alkyl groups having 1–4 carbon atoms, aryl groups having from 6–14 carbon atoms, aralkyl groups having 7–22 carbon atoms and alkylidene groups having 1–4 carbon atoms;

when W represents C=, m is 1, B is a group represented by the formula:

in which the double bond is coupled with W and $R_3$ represents a substituted or unsubstituted aryl group or a substituted or unsubstituted aralkyl group, wherein the substituents are selected from the group consisting of one or more of halogen atoms, alkyl groups having 1–4 carbon atoms, alkoxy groups having 1–4 carbon atoms and hydroxyl groups;

when W represents a nitrogen atom, m is 0 or 1, and B represents a carbonyl group, a sulfonyl group, an alkylene group, an alkenylene group or a group —CHR$_4$— in which R$_4$ represents a substituted or unsubstituted aryl group, wherein said aryl group may be substituted with one or more of halogen atoms, alkyl groups having 1–4 carbon atoms and alkoxy groups having 1–4 carbon atoms;

E$_1$ and E$_2$ each independently represents a hydrogen atom or a lower alkyl group;

D represents a substituted or unsubstituted aromatic hydrocarbon group or a substituted or unsubstituted aromatic heterocyclic group, wherein said group may be substituted with one or more of halogen atoms, alkyl groups having 1–4 carbon atoms, alkoxy groups having 1–4 carbon atoms, aryl groups having 6–14 carbon atoms, aralkyl groups having 7–22 carbon atoms, aralkyloxy groups having 7–22 carbon atoms, cyano groups, nitro groups, carboxyl groups, alkoxycarbonyl groups, lower alkylsulfonylamino groups, carbamoyl groups and hydroxy groups; and R represents a hydrogen atom, a linear or branched alkyl group, a cycloalkyl group, a cycloalkyl-alkyl group or a substituted or unsubstituted aralkyl group, wherein said aralkyl group maybe substituted with one or more of halogen atoms, alkyl groups having 1–4 carbon atoms and alkoxy groups having 1–4 carbon atoms.

17. A process for the preparation of a compound represented by formula (Ii) or (Ii'):

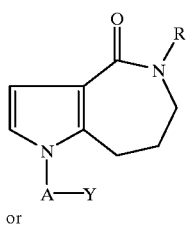
(Ii)

or

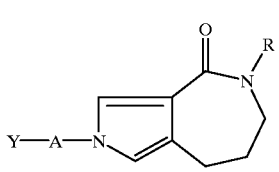
(Ii')

comprising:

dehydrating a compound represented by formula (Ih) or (Ih'):

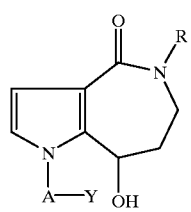
(Ih)

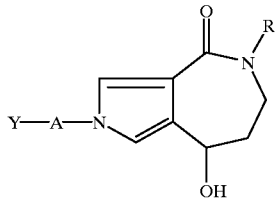
(Ih')

wherein

A represents an alkylene group, an alkenylene group or an alkynylene group;

Y is a group represented by the formula:

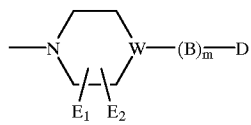

in which

W represents CH, C= or a nitrogen atom; and, when W represents CH, m is 0 or 1, B represents an oxygen atom, a sulfur atom, a carbonyl group, a sulfinyl group, a sulfonyl group, an alkylene group, an alkenylene group, a group —C(OH)R$_1$— in which R$_1$ represents a substituted or unsubstituted aryl group, wherein the substituents are selected from the group consisting of alkyl groups having 1–4 carbon atoms and aryl groups having 6–14 carbon atoms, wherein said alkyl and aryl groups may be substituted with one or more of halogen atoms, alkoxy groups having 1–4 carbon atoms, hydroxyl groups, cyano groups and nitro groups, a group —CHR$_2$— in which R$_2$ represents a substituted or unsubstituted aryl group, wherein said aryl group may be substituted with one or more of halogen atoms, alkoxy groups having 1–4 carbon atoms, hydroxyl groups, cyano groups and nitro groups, or a substituted or unsubstituted, cyclic or acyclic acetal group, wherein said group may be substituted with one or more of halogen atoms, alkyl groups having 1–4 carbon atoms, aryl groups having from 6–14 carbon atoms, aralkyl groups having 7–22 carbon atoms and alkylidene groups having 1–4 carbon atoms;

when W represents C=, m is represented by the formula:

in which the double bond is coupled with W and R$_3$ represents a substituted or unsubstituted aryl group or a substituted or unsubstituted aralkyl group, wherein the substituents are selected from the group consisting of one or more of halogen atoms, alkyl groups having 1–4 carbon atoms, alkoxy groups having 1–4 carbon atoms and hydroxyl groups;

when W represents a nitrogen atom, m is 0 or 1, and B represents a carbonyl group, a sulfonyl group, an alkylene group, an alkenylene group or a group —CHR$_4$— in which R$_4$ represents a substituted or unsubstituted aryl group, wherein said aryl group may be substituted with one or more of halogen atoms, alkyl groups having 1–4 carbon atoms and alkoxy groups having 1–4 carbon atoms;

E$_1$ and E$_2$ each independently represents a hydrogen atom or a lower alkyl group; and D represents a substituted or unsubstituted aromatic hydrocarbon group or a substituted or unsubstituted aromatic heterocyclic group, wherein said group may be substituted with one or more of halogen atoms, alkyl groups having 1–4 carbon atoms, alkoxy groups having 1–4 carbon atoms, aryl groups having 6–14 carbon atoms, aralkyl groups having 7–22 carbon atoms, aralkyloxy groups having 7–22 carbon atoms, cyano groups, nitro groups, carboxyl groups, alkoxycarbonyl groups, lower alkylsulfonylamino groups, carbamoyl groups and hydroxy groups; and R represents a hydrogen atom, a linear or branched alkyl group, a cycloalkyl group, a cycloalkyl-alkyl group or a substituted or unsubstituted aralkyl group, wherein said aralkyl group may be substituted with one or more of halogen atoms, alkyl groups having 1–4 carbon atoms and alkoxy groups having 1–4 carbon atoms.

18. A process for the preparation of a compound represented by formula (Ij) or (Ij'):

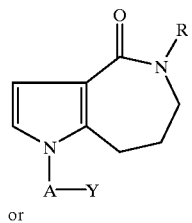
(Ij)

or

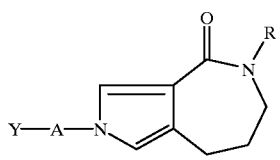
(Ij')

comprising:

reducing a compound represented by formula (XII) or (XII'):

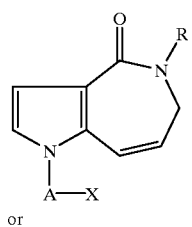
(XII)

or

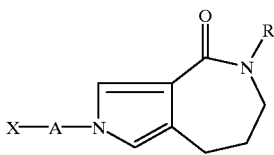
(XII')

to produce a compound represented by formula (XIII) or (XIII'):

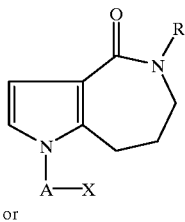
(XIII)

or

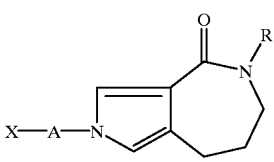
(XIII')

and then
reacting a nitrogen-containing compound represented by formula (V):

H—Y     (V)

with the compound represented by the formula (XIII) or (XIII'), wherein

A represents an alkylene group, an alkenylene group or an alkynylene group;

X is an eliminative group;

Y is a group represented by the formula:

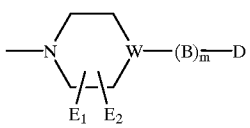

in which
W represents CH, C= or a nitrogen atom; and,
when W represents CH, m is 0 or 1, B represents an oxygen atom, a sulfur atom, a carbonyl group, a sulfinyl group, a sulfonyl group, an alkylene group, an alkenylene group, a group —C(OH)R$_1$— in which R$_1$ represents a substituted or unsubstituted aryl group, wherein the substituents are selected from the group consisting of alkyl groups having 1–4 carbon atoms and aryl groups having 6–14 carbon atoms, wherein said alkyl and aryl groups may be substituted with one or more of halogen atoms, alkoxy groups having 1–4 carbon atoms, hydroxyl groups, cyano groups and nitro groups, a group —CHR$_2$— in which R$_2$ represents a substituted or unsubstituted aryl group, wherein said aryl group may be substituted with one or more of halogen atoms, alkoxy groups having 1–4 carbon atoms, hydroxyl groups, cyano groups and nitro groups, or a substituted or unsubstituted, cyclic or acyclic acetal group, wherein said group may be substituted with one or more of halogen atoms, alkyl groups having 1–4 carbon atoms, aryl groups having from 6–14 carbon atoms, aralkyl groups having 7–22 carbon atoms and alkylidene groups having 1–4 carbon atoms;

when W represents C=, m is 1, B is a group represented by the formula:

in which the double bond is coupled with W and $R_3$ represents a substituted or unsubstituted aryl group or a substituted or unsubstituted aralkyl group, wherein the substituents are selected from the group consisting of one or more of halogen atoms, alkyl groups having 1–4 carbon atoms, alkoxy groups having 1–4 carbon atoms and hydroxyl groups;

when W represents a nitrogen atom, m is 0 or 1, and B represents a carbonyl group, a sulfonyl group, an alkylene group, an alkenylene group or a group —$CHR_4$— in which $R_4$ represents a substituted or unsubstituted aryl group, wherein said aryl group may be substituted with one or more of halogen atoms, alkyl groups having 1–4 carbon atoms and alkoxy groups having 1–4 carbon atoms;

$E_1$ and $E_2$ each independently represents a hydrogen atom or a lower alkyl group; and D represents a substituted or unsubstituted aromatic hydrocarbon group or a substituted or unsubstituted aromatic heterocyclic group, wherein said group may be substituted with one or more of halogen atoms, alkyl groups having 1–4 carbon atoms, alkoxy groups having 1–4 carbon atoms, aryl groups having 6–14 carbon atoms, aralkyl groups having 7–22 carbon atoms, aralkyloxy groups having 7–22 carbon atoms, cyano groups, nitro groups, carboxyl groups, alkoxycarbonyl groups, lower alkylsulfonylamino groups, carbamoyl groups and hydroxy groups; and R represents a hydrogen atom, a linear or branched alkyl group, a cycloalkyl group, a cycloalkyl-alkyl group or a substituted or unsubstituted aralkyl group, wherein said aralkyl group may be substituted with one or more of halogen atoms, alkyl groups having 1–4 carbon atoms and alkoxy groups having 1–4 carbon atoms.

19. A pharmaceutical composition, comprising a compound or a salt thereof according to claim 1 and a pharmaceutically acceptable extender or carrier.

20. A method of treating a circulatory disease selected from the group consisting of hypertension, heart failure, ischemic heart diseases, cerebrebral infarction, cerebral sequelae after subarachnoid hemorrhage, ateriosclerosis obliterans, thromboangiitis obliterans, Raynaud disease and Buerger disease, comprising administering an effective amount of a compound or a salt thereof according to claim 1 to a patient in need thereof.

21. A method of antagonizing serotonin-2 receptors, comprising administering an effective amount of a compound or a salt thereof according to claim 1 to a patient in need thereof.

* * * * *

UNITED STATES PATENT AND TRADEMARK OFFICE
CERTIFICATE OF CORRECTION

PATENT NO. : 6,187,772 B1
DATED : February 13, 2001
INVENTOR(S) : Akira Mizuno et al.

It is certified that error appears in the above-identified patent and that said Letters Patent is hereby corrected as shown below:

Column 51,
Line 67, "—C(OH)R—" should read -- —C(OH)$R_1$— --.

Column 53,
Line 49, "(VIa) or (VIIB);" should read -- (VIIa) or (VIIb): --.

Column 59,
Line 34, "(VIb):" should read -- (VIIb): --.

Column 74,
Line 23, "cerebrebral" should read -- cerebral --.
Line 24, "ateriosclerosis" should read -- arteriosclerosis --.

Signed and Sealed this

Twenty-third Day of October, 2001

Attest:

NICHOLAS P. GODICI
Attesting Officer   Acting Director of the United States Patent and Trademark Office